(12) United States Patent
Duzinkiewicz et al.

(10) Patent No.: US 12,416,972 B2
(45) Date of Patent: Sep. 16, 2025

(54) METHOD OF PERFORMING A USER-SPECIFIC AND DEVICE-SPECIFIC CALIBRATION OF POINT OF GAZE ESTIMATION

(71) Applicant: Eye Square GmbH, Berlin (DE)

(72) Inventors: Karol Duzinkiewicz, Banino (PL); Jan Glinko, Gdansk (PL); Artur Skrzynecki, Wejherowo (PL); Michael Schiessl, Berlin (DE); Cezary Polak, Gdynia (PL)

(73) Assignee: eye square GMBH, Berlin (DE)

( * ) Notice: Subject to any disclaimer, the term of this patent is extended or adjusted under 35 U.S.C. 154(b) by 0 days.

(21) Appl. No.: 18/757,384

(22) Filed: Jun. 27, 2024

(65) Prior Publication Data

US 2025/0004548 A1    Jan. 2, 2025

Related U.S. Application Data

(63) Continuation-in-part of application No. 18/345,911, filed on Jun. 30, 2023, now Pat. No. 12,229,992.

(51) Int. Cl.
*G06F 3/01* (2006.01)
*G06T 7/80* (2017.01)

(52) U.S. Cl.
CPC ............... *G06F 3/013* (2013.01); *G06T 7/80* (2017.01)

(58) Field of Classification Search
CPC ............ G06T 7/74; G06T 2207/20081; G06T 2207/20084; G06T 2207/30196; G06F 3/013
See application file for complete search history.

(56) References Cited

U.S. PATENT DOCUMENTS

| | | | |
|---|---|---|---|
| 10,884,494 B1 * | 1/2021 | Lagies | G06F 3/017 |
| 2018/0197336 A1 * | 7/2018 | Rochford | G06F 3/0481 |
| 2022/0050521 A1 * | 2/2022 | Drozdov | G06V 40/193 |
| 2022/0206571 A1 * | 6/2022 | Drozdov | G06V 40/161 |
| 2022/0236797 A1 * | 7/2022 | Drozdov | G06V 10/82 |
| 2024/0094808 A1 * | 3/2024 | Fu | G06F 3/013 |

* cited by examiner

*Primary Examiner* — Kenneth B Lee, Jr.
(74) *Attorney, Agent, or Firm* — Anooj Patel; Kevin Schraven; Hankin Patent Law, APC

(57) ABSTRACT

A method of performing a user-specific and device-specific calibration of point of gaze estimation comprising a user's mobile device, a calibration target displayer, a built-in camera video data recorder, a perspective transform matrix process, a calibration data set splitter, and a support vector regression calculator by having a built-in camera process gaze in absolute measurement terms based on a series of successive data points based on a non-static marker.

10 Claims, 19 Drawing Sheets

Calibration pipeline

Normal mode of operation pipeline

Frame #1 & $(x_{gt,1}, y_{gt,1})$

Frame #2 & $(x_{gt,2}, y_{gt,2})$

[...]

Frame #M & $(x_{gt,M}, y_{gt,M})$ $M$

Frame #M+1 & $(x_{gt,M+1}, y_{gt,M+1})$

[...]

Frame #N & $(x_{gt,N}, y_{gt,N})$

METHOD OF PERFORMING A USER-SPECIFIC AND DEVICE-SPECIFIC CALIBRATION OF POINT OF GAZE ESTIMATION

CROSS-REFERENCE TO RELATED APPLICATIONS

This Non-Provisional application claims the benefit of and priority to U.S. Provisional patent application Ser. No. 18/345,911, filed on Jun. 30, 2023, titled METHOD OF PERFORMING A USER-SPECIFIC AND DEVICE-SPECIFIC CALIBRATION OF POINT OF GAZE ESTIMATION, the contents of which are expressly incorporated herein by this reference as though set forth in their entirety and to which priority is claimed.

FIELD OF USE

The present disclosure relates generally to the field of point of gaze estimation. More specifically, the present disclosure relates to a method of performing a user-specific and device-specific calibration of point of gaze estimation where calibration data is collected and processed when a user responds to calibration targets displayed on the screen of the user's device.

BACKGROUND

Point of Gaze ("PoG") estimation pipeline is a set of algorithmic blocks that can estimate where a user is looking on a device's screen by using the input from a built-in camera that is facing the user. PoG is expressed as a 2D point (x, y) in millimeters in a screen coordinate system with origin in the top-left corner of the screen.

Usually this set of algorithmic blocks is based on machine learning technology, so its parameters may be obtained during a training process based on a large set of images that are sourced from different people. While the out-of-the-box PoG estimation pipeline with default settings may generally perform reasonably well on a wide range of users under normal circumstances, precision on the level that is often desirable requires additional user-specific & device-specific calibration to increase accuracy.

In many use cases the accuracy of PoG estimation is ideally to the degree of millimeters. Default parameters of an out-of-the-box PoG estimation pipeline with default settings will usually result in error on a level of tens of millimeters. While this may be adequate for some uses, higher degrees of accuracy are generally preferable.

Existing methods of calibration in the prior art usually require the user to look at a set of calibration points in order to calculate a set of mapping functions that are usually 2nd order polynomials. This is typically achieved by solving a least-square problem over a set of linear equations derived from calibration data. The output from this is a pair of mapping functions $f_x$ and $f_y$:

$$x_{fine,i} = f_x(x_{init,i}, y_{init,i})$$

$$y_{fine,i} = f_y(x_{init,i}, y_{init,i})$$

The goal is to have xfine, i≈xgt,i and yfine, i≈ygt,i.

Using this approach may give inadequate results because the relation between ($x_{init,i}$, $y_{init,i}$) and ($x_{gt,i}$, $y_{gt,i}$) is generally not well-modeled by 2nd order polynomials. Moreover, existing methods often use a predefined calibration target display pattern. This may cause the user to anticipate the subsequent calibration target location, which may cause the calibration input data to be biased.

The use of PoG estimation has a number of potential applications, many of which are hampered by degrees of accuracy that rather than allow the user to more easily navigate a device or allow systems to anticipate a user's needs cause more frustration to the user as the system attempts, and fails, to provide desired feedback. Instead, incorrect feedback may be provided to the user and cause the user frustration, which may lead to dissolution with adoption of new technology.

In light of all the aforementioned technologies and applications, there are significant limitations and there is a need for a method of performing a user-specific and device-specific calibration for point of gaze estimation where calibration data is collected and processed when a user responds to calibration targets displayed on the screen of the user's device.

SUMMARY OF THE INVENTION

To minimize the limitations in the cited references, and to minimize other limitations that will become apparent upon reading and understanding the present specification, the method of performing a user-specific & device-specific calibration of point of gaze estimation herein relates to a method of performing a user-specific and device-specific calibration of point of gaze estimation where calibration data is collected and processed when a user responds to calibration targets displayed on the screen of the user's device.

In the following description, certain terminology is used to describe certain features of the various embodiments of the device, method, and/or system. For example, as used herein, the terms "computer" and "computer system" generally refer to any device that processes information with an integrated circuit chip.

The approach provided in the present disclosure makes use of a completely random calibration target display pattern, so the user is unable to anticipate the next location of the calibration target, even if one repeats the calibration procedure many times.

Components of the Present Disclosure

Calibration Target Displayer:

A calibration target displayer may be used for displaying calibration targets (e.g., dots) on the device's screen in L different locations by a duration of M frames. Calibration targets may be displayed in random positions across the whole screen to cover different possible PoG locations. Calibration targets may have a form of red dots of approximately 1 mm in radius.

Built-In Camera Video Data Recorder:

A built-in camera video data recorder may be used for capturing image frames from a built-in user-facing camera of the user's device. Corresponding data describing what the calibration target's ground truth position ($x_{gt,i}$, $y_{gt,i}$) was in the device's screen coordinates for a given frame may be collected. In general, for each calibration target's ground truth position, there may be M corresponding frames. As used herein, this configuration may be referred to as a calibration data set C.

Default PoG Estimation Pipeline Runner:

A default PoG Estimation Pipeline Runner may comprise a PoG estimation pipeline with its default settings. It may take image frames ("i-th frames") from the calibration data set C, may pass them through the PoG estimation pipeline, and may collect outputs $(x_{init,i}, y_{init,i})$ for each i-th frame. The output from this element may be a set of [N=L*M] pairs of corresponding $(x_{gt,i}, y_{gt,i})$ and $(x_{init,i}, y_{init,i})$ values, which may be referred to as processed calibration data set C'.

Calibration Data Set Splitter:

A calibration data set splitter may be responsible for randomly splitting calibration data set into two (2) subsets: (1) training calibration data set T; and (2) validation calibration data set V. The initial calibration data set may be split using 70/30 ratio. The training calibration data set T may hold [0.7*L*M] data points, and the validation calibration data set V may hold [0.3*L*M] data points. In other embodiments, the data may be split in other ratios, and the calculations derived therefrom may be modified accordingly. In preferred embodiments the initial calibration data may be ratios wherein more data is placed in set T than V.

Support Vector Regression ("SVR") Calculator:

A support vector regression ("SVR") may use training calibration data set T and an SVR training algorithm to train an SVR model with given values of hyperparameters, C and γ. Assuming that there are Q possible values of C, and S possible values of γ, [Q*S] possible combinations may be obtained. SVR models may be trained for each of these combinations. When a collection of SVR models is trained, the validation calibration data set may be used to calculate $(x_{fine,i}, y_{fine,i})$ for each $(x_{init,i}, y_{init,i})$ for each trained SVR model. Then $(x_{fine,i}, y_{fine,i})$ may be compared with a corresponding $(x_{gt,i}, y_{gt,i})$ from the V set to calculate the Mean Absolute Error (MAE) across the entire V set. A preferred SVR model which implements a mapping function fSVR may then be selected as the one having the lowest MAE.

SVR models may be algorithms that may be chosen and tuned based on how tolerant of errors the system is permitted to be, preferably these tolerances are determined in such a way that the SVR models may continue to function as intended. Through acceptable error margin and through tuning tolerance of falling outside that acceptable error rate, a preferred SVR model may be selected for the appropriate application and calibration. In various circumstances, custom or specific SVR models may be generated for different use case scenarios or different applications.

In one embodiment, the selected SVR model may then be used to fine-tune the output of the default PoG estimation pipeline runner, running in normal mode of operation, using the following equation:

$$(x_{fine}, y_{fine}) = f_{SVR}(x_{init}, y_{init}).$$

Using SVR as provided in the present disclosure may have various benefits as compared to traditional calibration methods because SVR may often be a high-order non-linear model.

Principle of the Function of the Present Disclosure

A method of user-specific & device-specific calibration that may prompt or require a user to visually look at a series of calibration targets (e.g., dots or other shapes connoting a point or area) that are displayed on a device's screen in random positions over a period of time in a sequence (e.g. in one embodiment only one calibration target is visible at a given point in time) may allow for increased calibration accuracy. The calibration target may be displayed for a fixed amount of time (e.g., 1 second or other discrete time measurement), and then the calibration target may change position on the device's screen. In other embodiments, the fixed amount of time may be selected based on assumptions made about the user. For example, an application that is used for individuals having slower response times or impaired visual function may have a longer fixed amount of calibration time. In some embodiments, the system may adjust the calibration time based on input received from the user.

A video stream from the built-in user-facing camera may be captured while the user is prompted or required to look at a series of calibration targets. If an assumption is made that the user is looking precisely at the calibration targets when they are displayed on the screen, it can be determined where they are looking at a specific moment in time for an i-th video frame. For example, the ground truth position $(x_{gt,i}, y_{gt,i})$ may be known. In some embodiments, where an assumption is made that the user is trying to look directly at the target, but may fail for a known or unknown reason, the system may adjust the settings to collect more data or collect more data tolerant of deviations from what is expected.

A gaze estimation pipeline on the obtained video frames using the default parameters may then be used, and yield the PoG result $(x_{init,i}, y_{init,i})$ for each of those frames. Those initial results may have a deviation compared to $(x_{gt,i}, y_{gt,i})$ that can be calculated. The error $e_{init,i}$ for i-th frame may be calculated as L2 distance between $(x_{gt,i}, y_{gt,i})$ and $(x_{init,i}, y_{init,i})$:

$$e_{init,i} = \sqrt{(x_{gt,i} - x_{init,i})^2 + (y_{gt,i} - y_{init,i})^2}$$

The goal of the calibration procedure may be to find the best mapping function $f_{mapping}$:

$$(x_{fine,i}, y_{fine,i}) = f_{mapping}(x_{init,i}, y_{init,i}),$$

that may transform an initial PoG result $(x_{init,i}, y_{init,i})$ for i-th frame into a fine-tuned result $(x_{fine,i}, y_{fine,i})$ to minimize average error $AE_{fine}$ across all available video frames N:

$$AE_{fine} = \frac{1}{N}\sum_{i=1}^{N} e_{fine,i}.$$

Where i is the index of a video frame, and $$e_{fine,i} = \sqrt{(x_{gt,i} - x_{fine,i})^2 + (y_{gt,i} - y_{fine,i})^2}$$

After the calibration process is completed, the calculated mapping function may be used to fine-tune outputs from the PoG estimation pipeline during normal mode of operation (e.g., when ground truth data is not available). These principles may be applied and explained as a series of steps.

Overview of the PoG Calibration Method

Generally, the calibration method may comprise a series of steps performed on an electronic device having a screen and a camera. In some embodiments, the camera may have a known location on the electronic device relative to the screen. In some embodiments, the screen and/or camera may be located on different devices. In one embodiment, the method may be performed on the electronic device itself. In another embodiment, the method may be performed on a separate device.

First, a set of calibration targets may be sequentially or non-sequentially displayed on the device's screen in random locations across the entirety of the screen, or a substantial portion of the screen, and prompt the user to focus their gaze on each target for a short period of time (e.g. 1 second duration for each location). In some embodiments, the short period of time may be adjusted in order to account for different users with different reaction times. In some embodiments, the short period of time may be adjusted during calibration based on feedback received.

Second, while the calibration target is displayed at a given position, M video frames may be captured from a built-in user-facing camera, and that video frame capture may be linked to the displayed calibration target locations, i.e., the ground truth data. In some embodiments, the camera determining the user's eye movements and/or position may be separate from the display device. In some embodiments, only a single video frame or photograph may be captured. In other embodiments the number of video frames captured may be substantially any amount, with an upper limit defined by the hardware used to capture video frames.

This may create a calibration data set C in which $(x_{gt,1}, y_{gt,1})=(x_{gt,2}, y_{gt,2})= \ldots =(x_{gt,M}, y_{gt,M})$; $(x_{gt,M+1}, y_{gt,M+1})=(x_{gt,M+2}, y_{gt,M+2})= \ldots =(x_{gt,M+M}, y_{gt,M+M})$, etc. If it is assumed that the calibration target will be displayed in L different locations, then N=L*M video frames with corresponding ground truth data may be obtained.

Third, all video frames from C using default gaze estimation pipeline may then be processed. In some embodiments, a subset of video frames from C using default gaze estimation pipeline may be processed. This may entail taking the frames to be processed as an input and output estimated PoG $(x_{init,i}, y_{init,i})$ for each i-th frame, creating a processed calibration set C'. In one embodiment, the creation of C' will mean that the video frames no longer need to be held for additional processing.

Fourth, C' may be divided into 2 subsets: (1) training set T (of length P), and (2) validation set V (of length R). In some embodiments, additional subsets may be created for specific reasons or purposes. T and V may be calculated by selecting mutually exclusive subsets of calibration target locations. For example, if the calibration target was displayed in L=5 different locations, data may be selected that corresponds to locations 1, 3 and 5 for T, and to locations 2 and 4 for V respectively.

Fifth, the T set may be used to train a Support Vector Regression (SVR) model with a Radial Basis Function (RBF) kernel, and the V set may be used to check against overfitting to the T set.

SVR is an extension of the Support Vector Classification (SVC), an algorithm that is widely used to find a mapping function for given data points. SVR may use the same concepts as SVC but may enable the user to find a mapping function between a set of features and continuous target values. In order to train an SVR model in the supervised manner, it may need to be fed with a set of training vectors (i.e. it may contain a set of initial PoG results $(x_{init,i}, y_{init,i})$ for each video frame) and a corresponding set of target values (i.e. it may contain a set of ground truth PoG locations $(x_{gt,i}, y_{gt,i})$).

The method may then iteratively look for an optimal mapping function that takes into consideration hyperparameter C and a cost function. The cost function may have many forms, but, generally, the most flexible function is the RBF kernel. It may be calculated using the following formula:

$$RBF(x_{gt}, x_{fine}) = \exp(-\gamma \cdot \|x_{gt} - x_{fine}\|^2)$$

In this embodiment, $\gamma$ must be greater than 0.

Hyperparameter C may balance an algorithm between high precision and complexity of the decision surface. A low C may make the decision surface smooth, while a high C aims at classifying all training examples correctly. $\gamma$ defines how much influence a single training example has. The larger $\gamma$, the closer other examples must be to be affected.

C and $\gamma$ values may need to be set accordingly. The optimal values may not be known up front, and a grid search is performed over a range of C and $\gamma$ values to pick the best combination. For a given combination of C and $\gamma$ values, an SVR model may be trained, and then the SVR model may be tested on the validation set by calculating mean absolute error (MAE) between the output of SVR model $(x_{fine,i}, y_{fine,i})$ and actual PoG locations in the validation set $(x_{gt,i}, y_{gt,i})$.

Sixth, a specific SVR model may be picked based on a minimum MAE value that may be used for processing all future data by the gaze estimation pipeline. In some embodiments, this SVR model may be identified as an ideal or best SVR model. Other SVR models may also be picked depending on the purpose.

Fine-Tuning Calibration Based on a User-Specific Data

In one embodiment, Fine-Tuning Calibration Based On User-Specific Data ("User Data Specific Calibration" or "UDSC") may be divided into four general components: data preparation, customized gaze estimation neutral network, training process, and user specific calibration. In one embodiment, Model-Agnostic Meta-Learning ("MAML") may be used, in contrast to gradient backpropagation. In some embodiments, users may have specific features identified, including, inter alia, gender, skin color, eye shape, age, hair, background color, and lighting conditions.

As used herein, the following table may be used to identify components of the UDSC:

| Variable | Variable Term | Explanation |
| --- | --- | --- |
| T | Task | A group of images of the same user, taken in the short interval (usually extracted from one recording). Each image has its corresponding ground truth gaze vector. |
| S | Support set | In the training phase, a dataset, with use of which, inner optimization is performed. In the adaptation phase, this is calibration data. |
| Q | Query set | In the training phase, a dataset with use of which meta optimization is performed. Does not occur in the adaptation phase but might be considered as all data coming from a specific user (after calibration). |
| θ | Parameters | The parameters of a given neural network. |
| ∇ | Gradient | $\nabla_x F(x)$ means derivative of $F(x)$ with respect to x. |
| $f_{\theta i}$ | Neural network output | Neural network output, when its parameters are $\theta_i$; i points to a specific step in the algorithm, because parameters are being constantly updated. |
| $L(f_{\theta i})$ | Loss function | Loss function computed for neural network output at the moment i with respect to the ground truth of the same moment i. |
| α | Inner optimization learning ratio | Gradient scaling applied in the inner loop optimization (support set). |

| Variable | Variable Term | Explanation |
| --- | --- | --- |
| β | Meta optimization learning ratio | Gradient scaling applied in the outer loop (meta) optimization. |
| $w_i$ | Inner loop gradient scaling | Independent scaling factor for loss computed and accumulated in every inner step on the Query set. |

Data Preparation

First, one of any known methods of appearance-based gaze estimation input preprocessing may be used. Then, the preprocessed data may be split according to the following conventions: 1) All data points originating from the same person are extracted from the whole dataset and compiled; 2) If any of the differences identified in the task definition (i.e. gender, skin color, shape of the eyes, age, hair, background color or lighting conditions) occurs among the person-specific data, the data is further split to form tasks (groups of images without strong differences between them); and 3) Data from each single task is split into two (separate) subsets, a support set and query set. In one embodiment, the support set size may be smaller than the query set size. In one embodiment, the support set size must be smaller than the query set size.

Neural Network

In one embodiment, the neural network may be a modification of the L2CS-Net proposed by Abdelrahman et al. (2022). In this embodiment, all batch normalization layers may have been removed from the network to improve cross-dataset generalization capabilities. Feature extraction is done by a ResNet-18 (He et al., 2017) backbone.

Training Process

To train the neural network, one embodiment may use a MAML approach (Finn et al. 2017). To stabilize the training, a multi-step optimization process may be utilized based on the following steps:

1. Initialize the network with the weights θ;
2. While not done:
   a. Sample a task $T_i$ from the set of tasks T
   b. Split $T_i$ data to $S_i$ (support) and $Q_i$ query sets
   c. Copy the weights $\theta_i = \theta$
   d. For number-of-inner-steps-times:
      i. Evaluate $\nabla_{\theta_i} L(f_{\theta_i})$
      ii. Compute adapted parameters with inner optimizer:

$$\theta_i = \theta_i - a\nabla_{\theta_i} L(fd)$$

e. Update $\theta \leftarrow \theta - \beta \nabla_\theta \Sigma w_i L(f_{\theta_i})$ with meta optimizer where:

$$L(f_\theta) = \text{CrossEntropyLoss}(f_\theta)|_{Classification} + \text{MeanAbsoluteError}(f_\theta)|_{Regression},$$

w: weights vector for each inner-step loss, implementing the Multi Step Optimization (Antoniou et al., 2018).

$$CrossEntropyLoss(f_\theta) = \sum_{c=1}^{M} y_{o,c} \log(f_{\theta,o,c})$$

where:
M—number of classes
log—the natural logarithm
y—binary indicator if class label c is correct classification for observation o
$f_{\theta,o,c}$—predicted probability observation o is class c $$MeanAbsoluteError(f_\theta) = \frac{1}{N} \sum_{n=1}^{N} |y_n - f_{\theta,n}|$$

where:
N—number of observations
$y_n$—ground truth for an observation
$f_{\theta,n}$—predicted value for an observation Support (calibration) set size is preferably smaller than the query set size to more closely resemble real-world use-case scenarios. In the training process the support set size may be about 20 data points and query set size may be about 30 data points, respectively, which translates to about 50 data points per task.

Other parameters used for training include:
number of inner steps: 3
α: 0.00001
β: 0.00005
w: starting from 1/number of inner steps for each step ending with [0, 0, 1] in the favor of the last step (Antoniou et al., 2018).

In one embodiment, Stochastic Gradient Descent ("SGD") and ADAM optimizers may be used for inner optimization and meta optimization, respectively.

For each task, the neural network parameters may be copied, and this copy may be updated with respect to the loss function computed from the support set predictions for a given number of times. Next, the loss on the query set may be computed and, on the basis of this loss, the original parameters of the neural network may be updated. This step may be repeated for the given number of iterations to obtain convergence of the training.

User Specific Calibration

Before usage of the network trained as described above, a fine-tuning step is preferred, i.e., user specific calibration. This fine-tuning procedure comprises the following steps:

1. Initialize the network with the meta-trained parameters θ;
2. Obtain a set number of calibration samples, comprising a face image and ground truth gaze vector, from a single user;
3. For number-of-inner-steps-times:
   a. Evaluate $\nabla_\theta L(f_\theta)$
   b. Compute adapted parameters with inner optimizer:

$$\theta = \theta - a\nabla_\theta L(f_\theta)$$

where L is the same loss as used while training and a is a learning ratio (which may be different from training a). Number of inner steps in the calibration procedure may be different compared to training phase.

After fine-tuning, the neural network may be ready to be used with a specific user. In a preferred embodiment, a further calibration procedure may be used for each user before the neural network.

In a preferred embodiment, a sequential order is. First, data is prepared to be fed to the training process. Next, the neural network is wrapped into the training procedure (MAML) and then trained. Lastly, a calibration procedure is performed on the meta-trained neural network to fine-tune the network to the specific user. One benefit of this approach is that a lengthy training phase need only be performed once, and a fast calibration procedure is preferred for each user.

Various Embodiments of the Disclosed Systems

One embodiment may be a method of performing a user-specific and device-specific calibration of point of gaze estimation comprising a user's mobile device, a calibration target displayer, a built-in camera video data recorder, a default Point of Gaze estimation pipeline runner, a calibration data set splitter, and a support vector regression calculator. Where the user's mobile device further comprises a built-in user-facing camera and a screen. Wherein the calibration target displayer displays a calibration target, where the calibration target changes position on the screen over a period of time, and where the various coordinates of the calibration target on the screen are recorded as target ground truth position data. A user tracks the position of the calibration target with their eyes. The built-in video data recorder captures frames of the user tracking the position of the calibration target with their eyes, and the target ground truth position data is matched with corresponding captured frames of the user tracking the position of the calibration target with their eyes to create a calibration data set. The calibration data set is processed by the default Point of Gaze estimation pipeline runner to collect PoG output data that corresponds to the target ground truth position data, where the target ground truth position data and PoG output data create a processed calibration data set. The processed calibration data set is split by the calibration data set splitter into a training calibration data set and a validation calibration data set. The support vector regression calculator processes the training calibration data set through several SVR training algorithms, where the several SVR training algorithms produce several SVR models after processing the training calibration data set. The validation calibration data set may be used to calculate preliminary positional gaze data for each of the several SVR models, where the preliminary gaze data can be compared against the validation calibration data set to calculate a mean absolute error for each data point of the validation calibration data set. The best SVR model is determined from the several SVR models based on the individual SVR model with a lowest mean absolute error, and the best SVR model fine-tunes the preliminary gaze data.

In another embodiment, the calibration target on the screen changes positions at random. In another embodiment, the change in position of the calibration target over the period of time is sequential. In another embodiment, the calibration target is a dot. In another embodiment, the calibration target is one millimeter in radius. In another embodiment, the captured frames of the user tracking the position of the calibration target with their eyes may be more than one frame.

In another embodiment, the training calibration data set and the validation calibration data set are split by the calibration data set splitter into an approximately 70/30 ratio, respectively.

In a preferred embodiment, all hardware components are contained in, and all steps are performed on, a single device. In alternate embodiments, hardware components may be contained on different devices, and/or steps may be performed on different devices. In one embodiment, the display and camera may be contained on a first device, and the data generated therefrom may be sent or transmitted, at any time, to a second device, wherein the second device may perform the various steps and calculations, and processed data, at any time, may be received by the first device for usage or further processing. In some embodiments, the processes may be split amongst other devices.

In some embodiments, multiple users may have their gaze calibrated, such as a situation wherein multiple people are in the same room, and multiple people are being prompted to focus on a series of points on a screen to calibrate the screen.

The various features and embodiments may be combined in multiple combinations so that any feature in the disclosure may be present in any combination of disclosure elements.

Other features and advantages inherent in the disclosed system and method for delivery metric analysis and notification, besides those which are claimed and disclosed, will become apparent to those skilled in the art from the following detailed description and its accompanying drawings.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps, which are illustrated. When the same numeral appears in different drawings, it refers to the same or like components or steps.

DETAILED DESCRIPTION OF THE DRAWINGS

Figure 1:
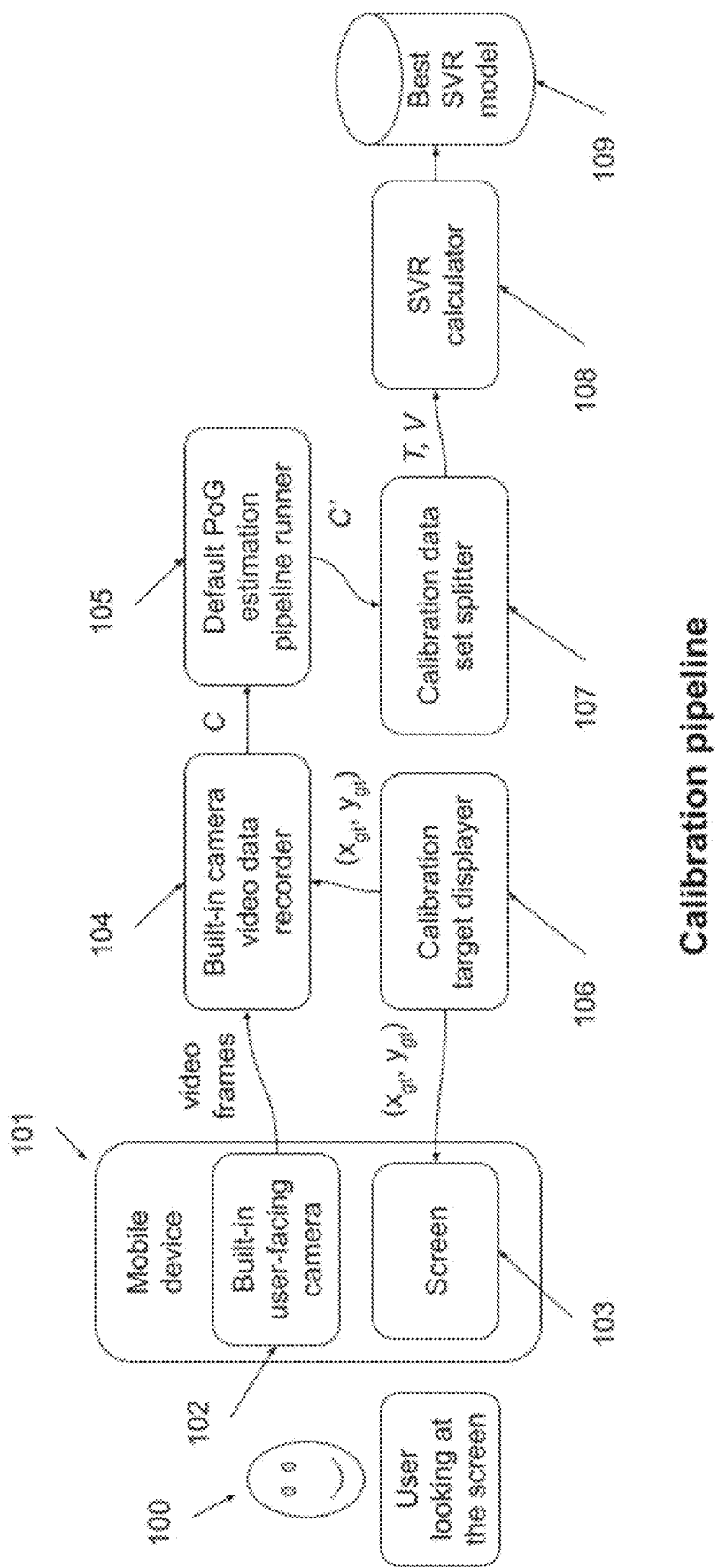
FIG. 1 is a diagram of one embodiment of a calibration pipeline employed by the present disclosure that yields a preferred SVR model.

In the following detailed description, numerous specific details are set forth in order to provide a thorough understanding of various aspects of one or more embodiments. However, these embodiments may be practiced without some or all of these specific details. In other instances, well-known methods, procedures, and/or components have not been described in detail so as not to unnecessarily obscure aspects of embodiments.

While multiple embodiments are disclosed, still other embodiments will become apparent to those skilled in the art from the following detailed description. As will be realized, these embodiments are capable of modifications in various obvious aspects, all without departing from the spirit and scope of protection. Accordingly, figures and the detailed descriptions thereof are to be regarded as illustrative in nature and not restrictive. Also, the reference or non-reference to a particular embodiment shall not be interpreted to limit the scope of protection.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about," may refer to a deviance of between 0.0001-40% from the indicated number or range of numbers.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

As will be appreciated by one skilled in the art, the systems and methods may take the form of an entirely hardware embodiment, an entirely software embodiment, or an embodiment combining software and hardware embodiments. Furthermore, the systems and methods may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, compact discs, read-only-memory (CD-ROMs), optical storage devices, or magnetic storage devices.

Embodiments of the systems and methods are described below with reference to schematic diagrams, block diagrams, and flowchart illustrations of methods, systems, apparatuses and computer program products. It will be understood that each block of the block diagrams, schematic diagrams, and flowchart illustrations, and combinations of blocks in the block diagrams, schematic diagrams, and flowchart illustrations, respectively, may be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, may be implemented by special purpose hardware-based computer systems that perform the specified functions or steps, or combinations of special purpose hardware and computer instructions.

In the following description, certain terminology is used to describe certain features of the various embodiments of the device, method, and/or system. For example, as used herein, the terms "computer" and "computer system" generally refer to any device that processes information with an integrated circuit chip and/or central processing unit (CPU).

As used herein, the terms "software" and "application" refer to any set of machine-readable instructions on a machine, web interface, and/or computer system" that directs a computer's processor to perform specific steps, processes, or operations disclosed herein.

As used herein, the term "computer-readable medium" refers to any storage medium adapted to store data and/or instructions that are executable by a processor of a computer system. The computer-readable storage medium may be a computer-readable non-transitory storage medium and/or any non-transitory data storage circuitry (e.g., buggers, cache, and queues) within transceivers of transitory signals. The computer-readable storage medium may also be any tangible computer readable medium. In various embodiments, a computer readable storage medium may also be able to store data, which is able to be accessed by the processor of the computer system.

As used herein, the terms "device", "computer", "computer system", "electronic data processing unit", and "server" refer to any device that processes information with an integrated circuit chip, including without limitation, personal computers, mainframe computers, workstations, servers, desktop computers, portable computers, laptop computers, embedded computers, wireless devices including cellular phones, personal digital assistants, tablets, tablet computers, smart phones, portable game players, wearables, smart devices and hand-held computers. The term "internet" refers to any collection of networks that utilizes standard protocols, whether Ethernet, Token ring, Wi-Fi, asynchronous transfer mode (ATM), Fiber Distributed Data Interface (FDDI), code division multiple access (CDMA), global systems for mobile communications (GSM), long term evolution (LTE), or any combination thereof. The term "website" refers to any document written in a mark-up language including, but not limited to, hypertext mark-up language (HTML) or virtual reality modeling language (VRML), dynamic HTML, extended mark-up language (XML), wireless markup language (WML), or any other computer languages related thereto, as well as to any collection of such documents reachable through one specific Internet Protocol Address or at one specific World Wide Web site, or any document obtainable through any particular Uniform Resource Locator (URL). Furthermore, the terms "webpage," "page," "website," or "site" refers to any of the various documents and resources on the World Wide Web, in HTML/XHTML format with hypertext links to enable navigation from one page or section to another, or similar such resources used on the Internet.

As used herein, the term "sender" refers to the valid author or transmitting user of a share, digital asset, file, link, content or resource from their mobile or fixed computing device. The sender configures the asset, and its security context factors, as well as chooses the parameters including timing, synchronicity, lifespan, access payment/fee and target recipients as well as the method or mode of transmission.

As used herein, the term "recipient" refers to the valid peer receiver, consumer, purchaser or engaging user of a sender's share, digital asset, file, link, content or resource on their mobile computing device. The recipient accesses a share on their device from any possible engagement channel and is authenticated and authorized via peer payment to the sender by the present device, system, and/or method according to their local and share global fees and policies set by the sender. The recipient is allowed, denied or misdirected access to the share source content or asset based on passage or failure to authenticate in context, execute the peer payment for the access or any other parameter required or set by the sender. The recipient can, in turn, become their own sender/seller of the same or a new content from their mobile device to other recipients. There may be one or more recipients.

As used herein, the terms "share" or "asset" refer to one or more, or a collection of one or more, encrypted or unencrypted hyperlinks, digital files, documents, images, sound or video files, streams, payments, events, downloads, locations or directions, communication, messages, tweets, posts, emails, short codes, apps or games or game events, knowledge, performance or other electronic manifestation of content capable of being authored, saved, stored, hosted, referenced, downloaded, transmitted and accessed, consumed, opened or otherwise engaged from a computing device according to the steps of the present method.

As used herein, the terms "secured share" or "secured asset" refer to an encrypted or unencrypted asset, file, or hyperlink that offers abstraction and indirection from the original protected source file, link, or asset and is used to transmit from sender to user in lieu of the original asset. The secured share link calls up the system processing when clicked or tapped on a mobile computing device for purposes of allowing or denying access according to the share and user context.

The terms "host" or "platform" refers to any computer network, platform, website or app infrastructure for public or private registration, connection, communication, hosting, sharing, streaming, access or presentation/publication of content, messages, information, data, files, streams, media, documents or computer code by users accessing from either fixed or mobile computing devices. Such "hosts" or "platforms" may include, but are not limited to, popular networks such as Facebook®, Instagram®, Yahoo®, Twitter®, Dropbox®, Box®, Evernote®, Apple® iCloud®, iMessage®, Google Cloud®, Microsoft® OneDrive®, SkyDrive®, Skype®, public email, text messaging, SMS, a web server, an app server, a mobile apps, wearable platforms, local networks and storage, chat or instant messaging.

FIG. 1 is a diagram of the calibration pipeline employed by the present disclosure that yields a preferred SVR model 109. To initiate the calibration pipeline, a user 100 interacts with the calibration target displayer 106 on the screen 103 of their mobile device 101, having a user-facing camera. The calibration target displayer displays calibration targets (i.e., dots) on the device's screen in L different locations by a duration of M frames. Calibration targets may be displayed in random positions across the whole screen to cover different possible PoG locations. Calibration targets may have a form of red dots of approximately 1 mm in radius. As the calibration target displayer 106 shows targets, corresponding data describing what the calibration target's ground truth position ($x_{gt,i}$, $y_{gt,i}$) was in the device's screen coordinates for a given frame is collected. As the calibration target displayer 106 displays calibration targets on the screen 103, the user 100 will then look at the targets, video frames of the user's 100 feedback to visually tracking the targets is collected by the device's built-in camera video data recorder 104. These video frames are combined with the calibration target's ground truth position ($x_{gt,i}$, $y_{gt,i}$), resulting in calibration data set C.

Calibration data set C is then run through a default PoG estimation pipeline runner 105. The default PoG estimation pipeline runner 105 takes image frames from the calibration data set C, passes them through the PoG estimation pipeline, and may collect outputs ($x_{init,i}$, $y_{init,i}$) for each i-th frame. The output from this element may be a set of [N=L*M] pairs of corresponding ($x_{gt,i}$, $y_{gt,i}$) and ($x_{init,i}$, $y_{init,i}$) values, which may be referred to as processed calibration data set C'.

Processed calibration data set C' is then run through the calibration data set splitter 107, which randomly splits the calibration data set into 2 subsets: (1) training calibration data set T; and (2) validation calibration data set V. The initial calibration data set may be split using 70/30 ratio but may be modified to other ratios that process the data more ideally.

Training calibration data set T and validation calibration data set V is then run through an SVR calculator 108, which uses training calibration data set T and an SVR training algorithm to train an SVR model with given values of hyperparameters, C and γ. Assuming that there are Q possible values of C, and S possible values of γ, [Q*S] possible combinations may be obtained. SVR models may be trained for each of these combinations. When a collection of SVR models is trained, the validation calibration data set may be used to calculate $(x_{fine,i}, y_{fine,i})$ for each $(x_{init,i}, y_{init,i})$ for each trained SVR model.

Then $(x_{fine,i}, y_{fine,i})$ may be compared with a corresponding $(x_{gt,i}, y_{gt,i})$ from the V set to calculate the Mean Absolute Error (MAE) across the entire V set. The best SVR model which implements a mapping function $f_{SVR}$ may then be selected as the one with the lowest MAE.

SVR models are algorithms that may be chosen and tuned based on how tolerant of errors the system is permitted to be. Through acceptable error margin and through tuning tolerance of falling outside that acceptable error rate, an ideal, or best SVR model 109 may be selected for the appropriate application and calibration.

The best SVR model 109 may then be used to fine-tune the output of the default PoG estimation pipeline runner, running in normal mode of operation.

Figure 2:
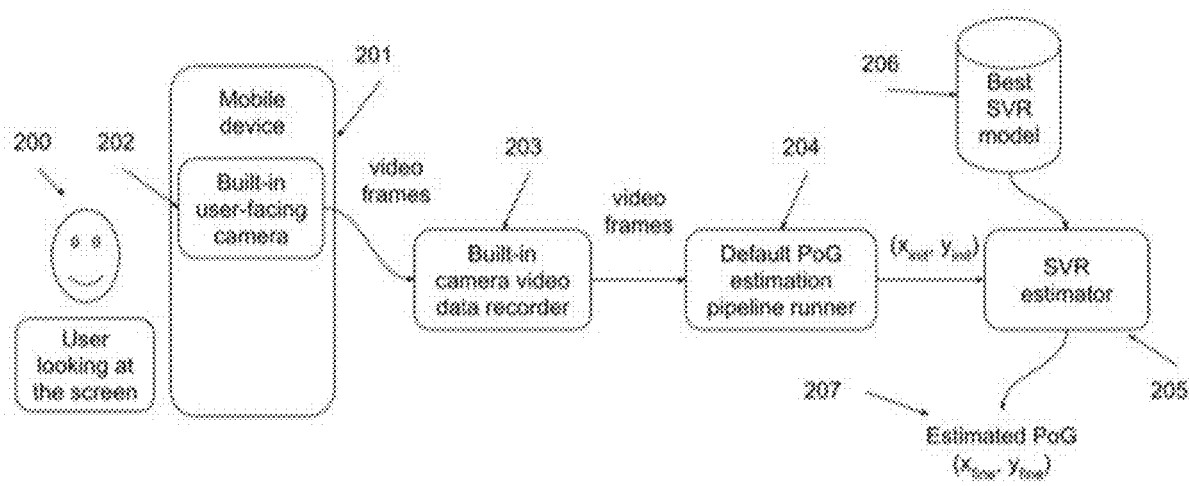
FIG. 2 is a diagram of one embodiment of the operation pipeline applying the preferred SVR model to yield the estimated PoG.

FIG. 2 is a diagram of one mode of the operation pipeline that applied the preferred SVR model to yield the estimated PoG. As a user 200 interacts with their device 201, having a user-facing camera 203, video frames of the user's 200 interaction with the device 201 is collected by the built-in user-facing camera 202 to generate and Estimated PoG 207. The video frames are then run through the default PoG estimation pipeline runner 204, which collects outputs $(x_{init,i}, y_{init,i})$ for each i-th frame. This data is then combined with the determined best SVR model 206 and run through an SVR estimator 205 to yield the estimated PoG, collected as data $(x_{fine}, y_{fine})$. The best SVR model 206 may then be used to fine-tune the output of the default PoG estimation pipeline runner, running in normal mode of operation, using the following equation:

$$(x_{fine}, y_{fine}) = f_{SVR}(x_{init}, y_{init}).$$

Figure 3:
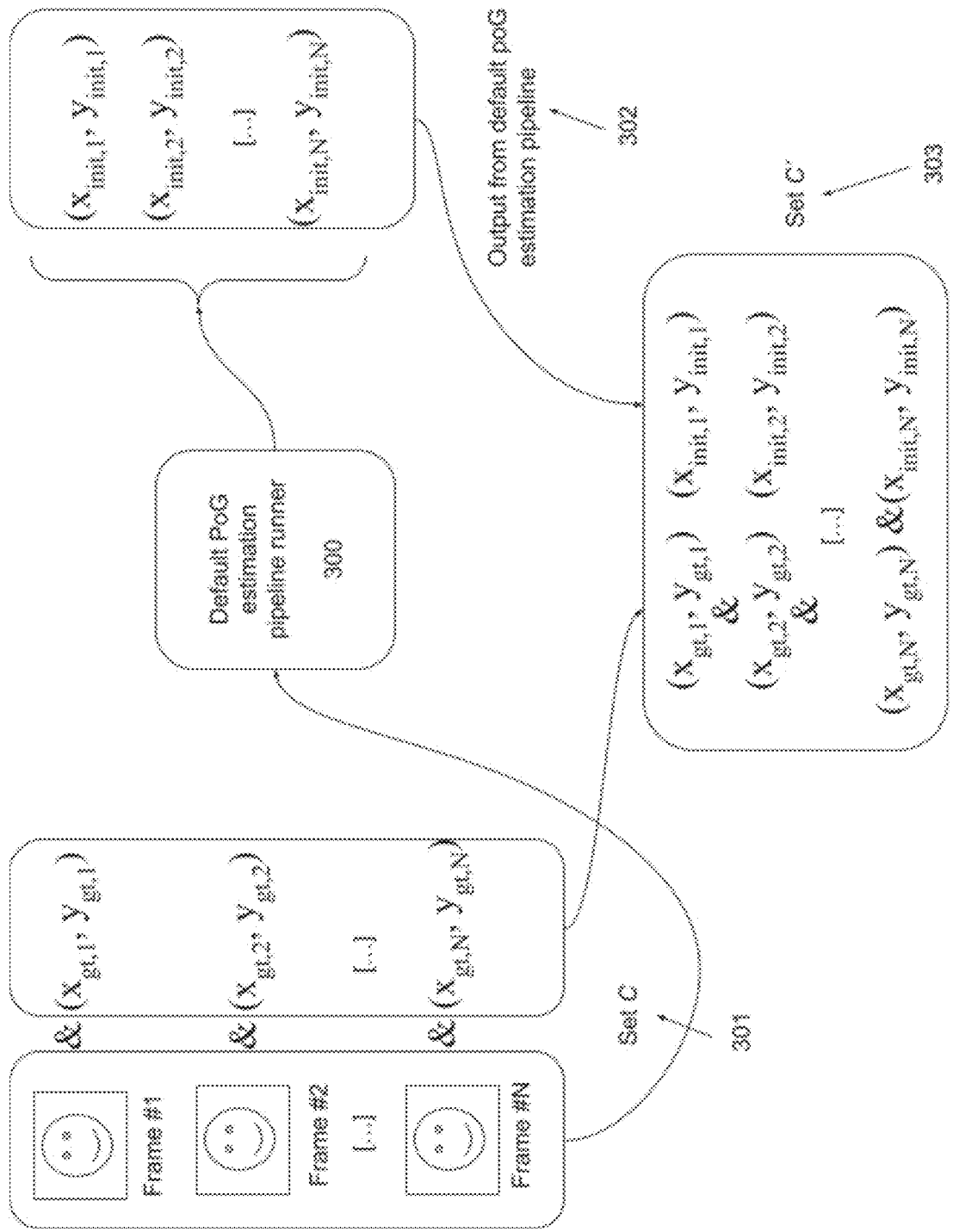
FIG. 3 is a diagram of one embodiment of the PoG estimation pipeline runner.

FIG. 3 is a diagram of one embodiment of the PoG estimation pipeline runner 300. First, the calibration target displayer and built-in camera video data record both collect data. The calibration target displayer displays calibration targets on the device's screen in L different locations by a duration of M frames. Corresponding data describing what the calibration target's ground truth position $(x_{gt,i}, y_{gt,i})$ was in the device's screen is collected. These coordinates are paired with corresponding image frames captured by the built-in camera video data recorder that captures image frames from the built-in user-facing camera of the user's device as the user reacts to the targets and provides visual feedback. In general, for each calibration target's ground truth position, there will be M corresponding frames. This will be called a calibration data set C 301.

The ground truth position coordinates are set aside for processed calibration data set C'. The image frames captured by the built-in camera video data recorder that captures image frames from the built-in user-facing camera of the user's device are run through the default PoG estimation pipeline runner 300 to yield outputs $(x_{init,i}, y_{init,i})$ for each i-th frame. This is the output from the default PoG estimation pipeline 302. The output from the default PoG estimation pipeline runner 300 may be a set of [N=L*M] pairs of corresponding $(x_{gt,i}, y_{gt,i})$ and $(x_{init,i}, y_{init,i})$ values, which may be referred to as processed calibration data set C' 303.

Figure 4:
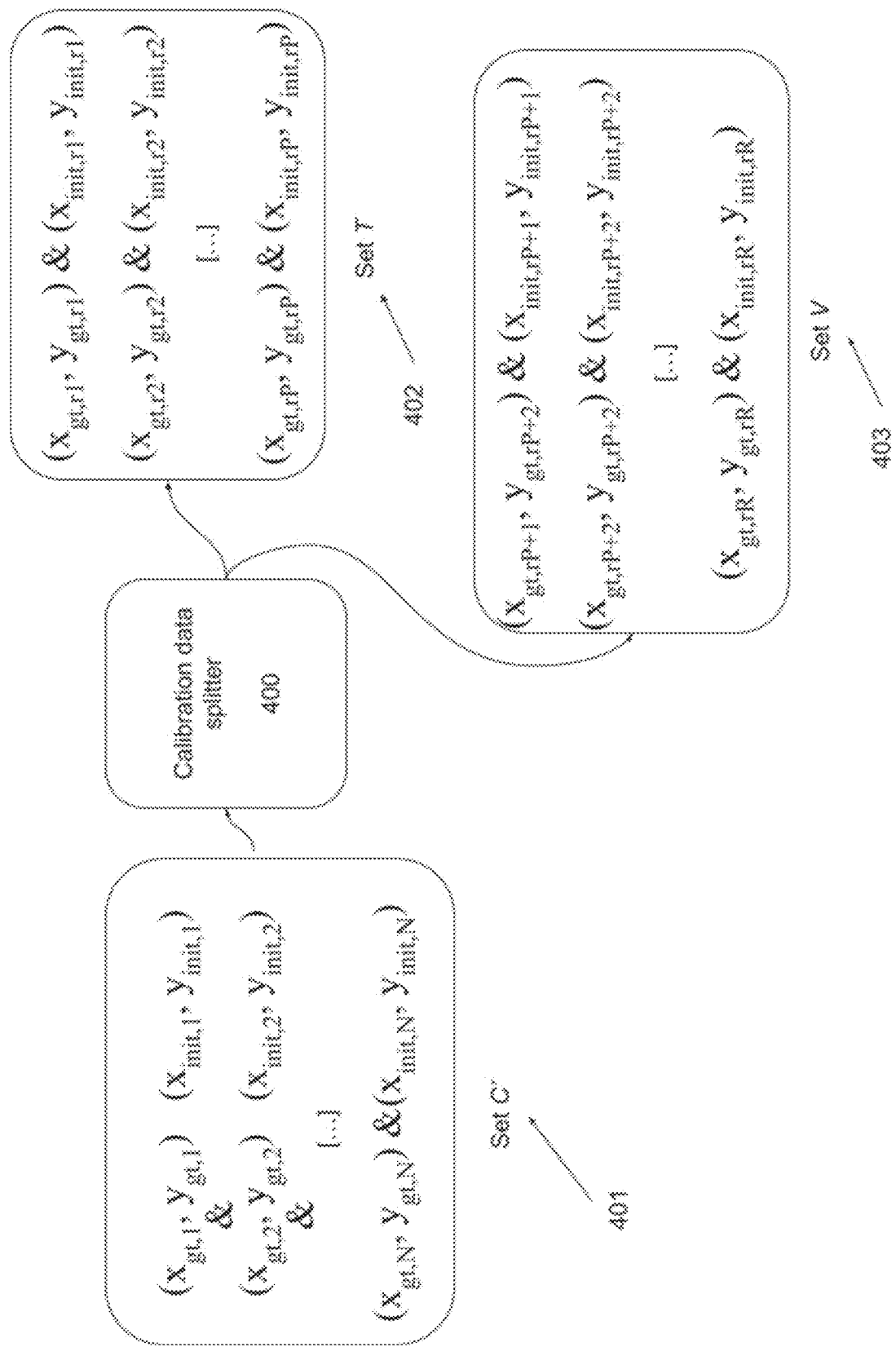
FIG. 4 is a diagram of one embodiment of a calibration data splitter.

FIG. 4 is a diagram of one embodiment of a calibration data splitter 400. Processed calibration data set C' 401 is run through the calibration data splitter 400 to yield (1) training calibration data set T 402 and (2) validation calibration data set V 403. The initial calibration data set may be split using 70/30 ratio, although the ratio may be altered at the initial point or at any other point during data processing if it may yield data more desirable to the data processor. The training calibration data set T 402 may hold [0.7*L*M] data points, and the validation calibration data set V 403 may hold [0.3*L*M] data points. The 0.7 and 0.3 in the two data sets may be adjusted to alternative proportions that add up to one if it may yield data more desirable to the data processor. Each of the two data sets are based off of the same set of ground truth positional data.

Figure 5:
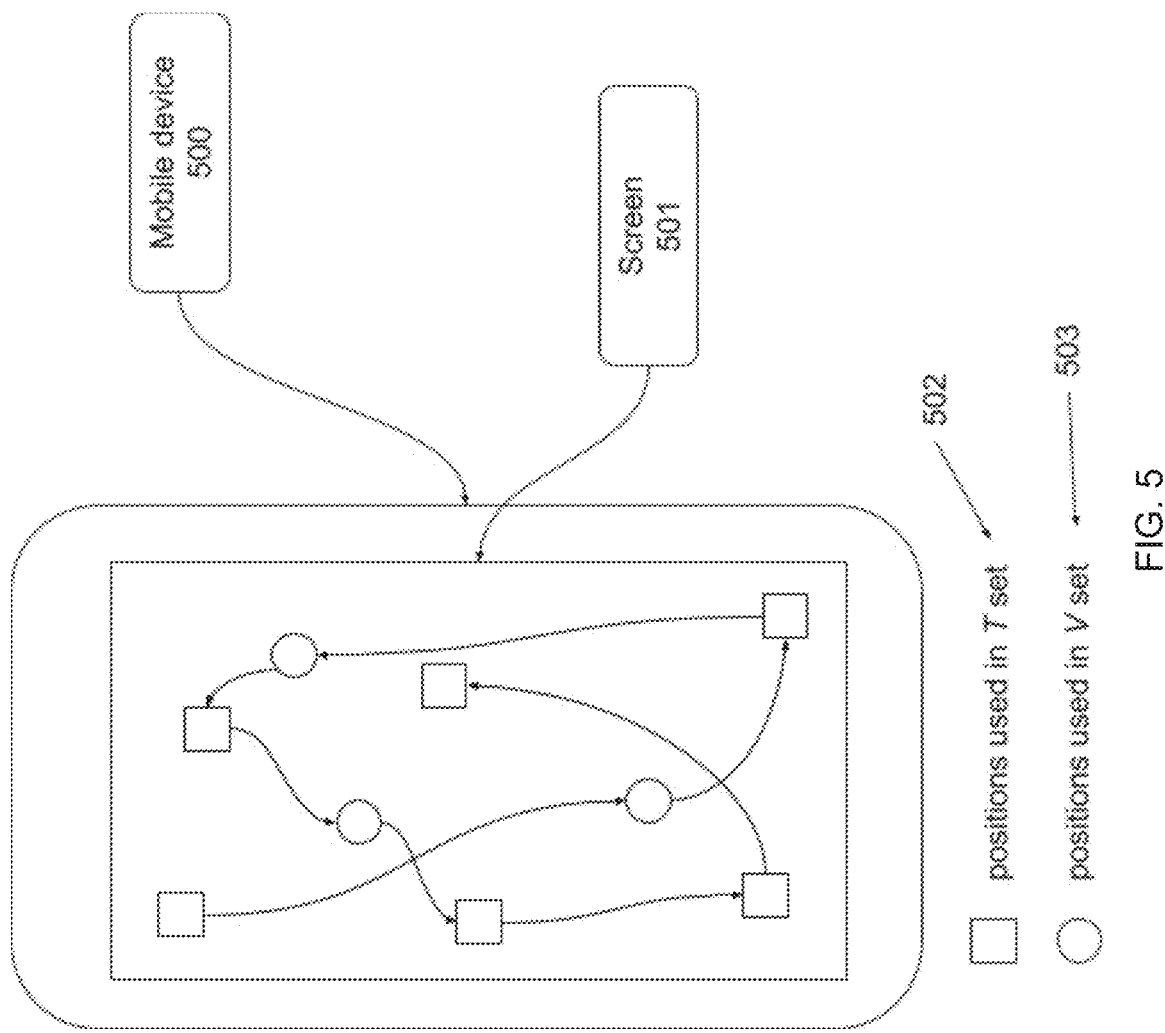
FIG. 5 is a diagram of one embodiment of random calibration patterns that may be used to obtain the train data set and validation data set.

FIG. 5 is a diagram of one embodiment of a random calibration pattern that may be used to obtain the train data set T 502 and validation data set V 503. As the user looks that screen 501 of their mobile device 500 during the calibration target display, the targets may be displayed sequentially in a random or non-random order. The ground truth positional data from the calibration target display is eventually proportionally split into the train data set T 502 and validation data set V 503. The ratio used to proportionally split the ground truth positional data into the two data sets may be predetermined or altered either at the start of data processing or at any point during data processing as desired by the processor.

Figure 6:
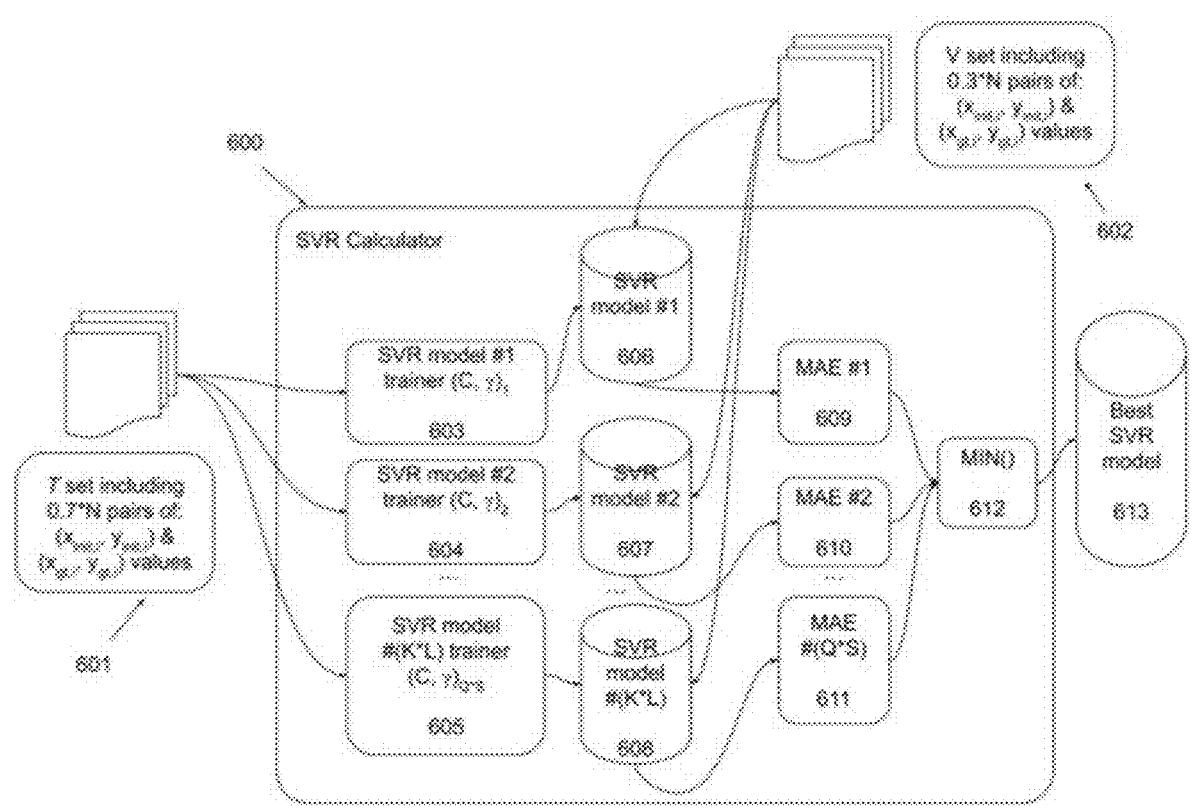
FIG. 6 is a diagram of one embodiment of the SVR calculator element of the present disclosure.

FIG. 6 is a diagram of the SVR calculator 600 element of the present disclosure. The training calibration data set T 601 is processed by the SVR calculator 600. The training calibration data set T 601 is run through SVR training algorithms 603, 604, 605 to further train SVR models 606, 607, 608 with given values of hyperparameters, C and γ. Assuming that there are Q possible values of C, and S possible values of γ, [Q*S] possible combinations may be obtained. SVR models 606, 607, 608 may be trained for each of these combinations.

Hyperparameter C may balance an algorithm between high precision and complexity of the decision surface. A low C may make the decision surface smooth, while a high C aims at classifying all training examples correctly. γ defines how much influence a single training example has. The larger γ, the closer other examples must be to be affected. C and γ values may need to be set accordingly. The optimal values may not be known up front, and a grid search is performed over a range of C and γ values to pick the best combination.

The SVR models 606, 607, 608 may be tested on the validation calibration set 602 by calculating mean absolute error ("MAE") 609, 610, 611 between the output of SVR model $(x_{fine,i}, y_{fine,i})$ and actual PoG locations in the validation set $(x_{gt,i}, y_{gt,i})$ 602.

The best SVR model 613 may be picked based on a minimum MAE value 612 that may be used for processing all future data by the gaze estimation pipeline.

Figure 7:
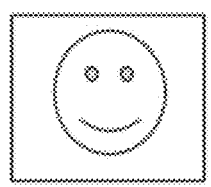
FIG. 7 is an illustration of a calibration data set.
Figure 7:
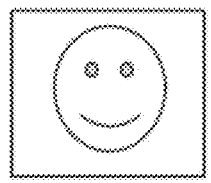
Figure 7:
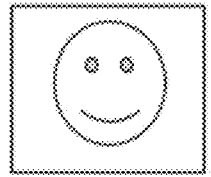
Figure 7:
Figure 7:
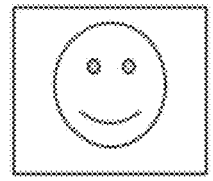
Figure 7:
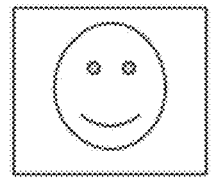

FIG. 7 is an illustration of a calibration data set. The calibration target displayer displays calibration targets on the device's screen in L different locations by a duration of M frames. Corresponding data describing what the calibration target's ground truth position $(x_{gt,i}, y_{gt,i})$ was in the device's screen is collected. These coordinates are paired with corresponding image frames captured by the built-in camera video data recorder that captures image frames from the built-in user-facing camera of the user's device as the user reacts to the targets and provides visual feedback. In general, for each calibration target's ground truth position, there will be M corresponding frames.

Figure 8:
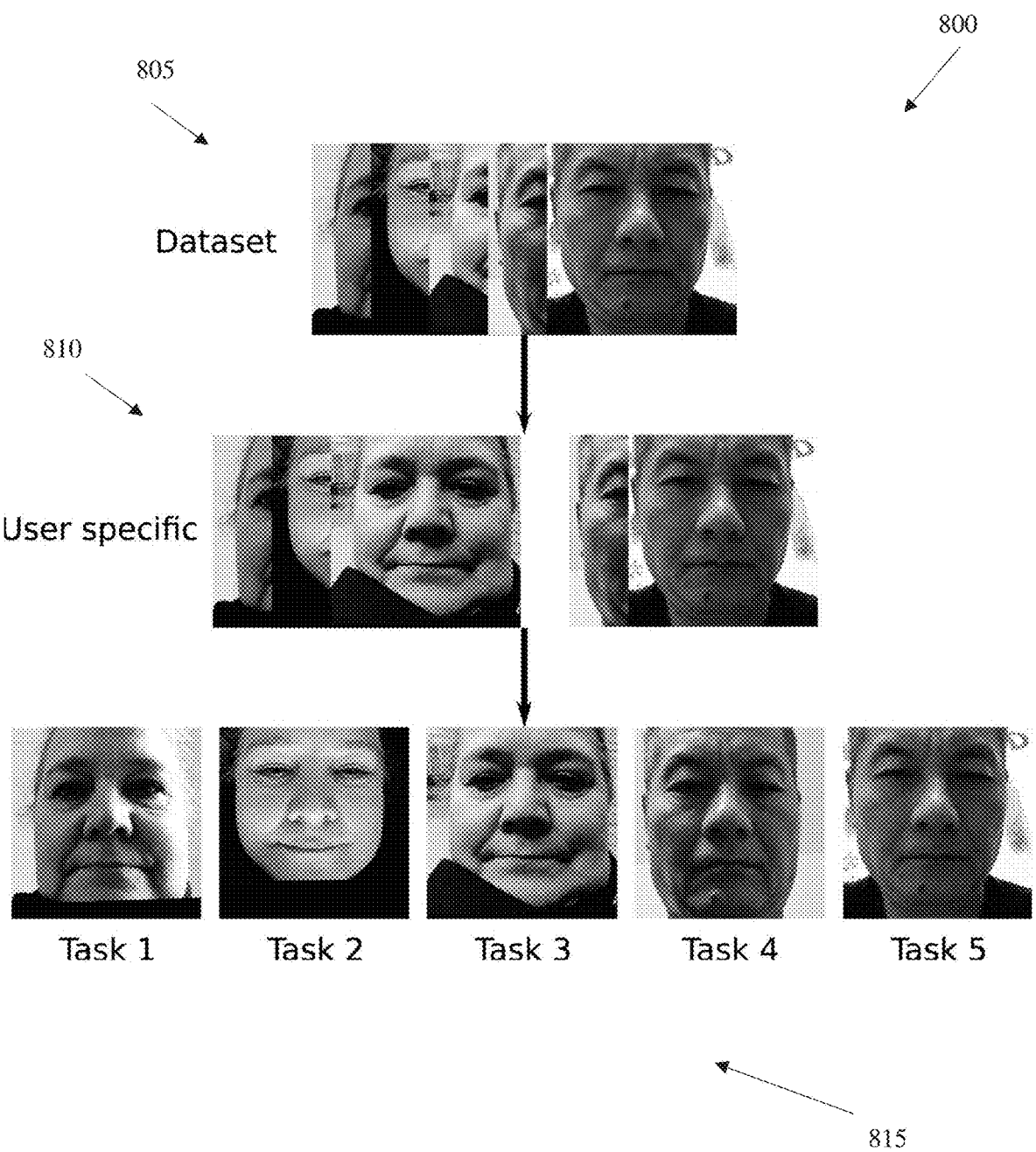
FIG. 8 is a diagram showing one embodiment of a data split pipeline, which shows that an initial dataset may be divided by user to be user specific, and which may then be further broken down into individual tasks comprising N images.

FIG. 8 is a diagram showing a data split pipeline 800. As shown, an initial dataset 805 may be divided by user to be user specific 810, which may then be further broken down into individual tasks 815, each of the tasks comprising N images. In one embodiment, each image has an annotation (ground truth) consisting of a gaze angle (pitch, yaw) vector. In alternate embodiments, other ways of annotating the images may be included.

In one embodiment, each task may be a set of images of the same person with similar conditions or characteristics, such as light conditions, background, glasses, and other detectable features. In other words, images of the same user will be split into different tasks if the images were taken in different places, at different times of the day, or if other conditions are present that affect the image. This sort of splitting or sorting may be beneficial to allow a neural network trained under the present disclosure to learn general features during the training phase and then task-specific features during the calibration phase.

Figure 9A:
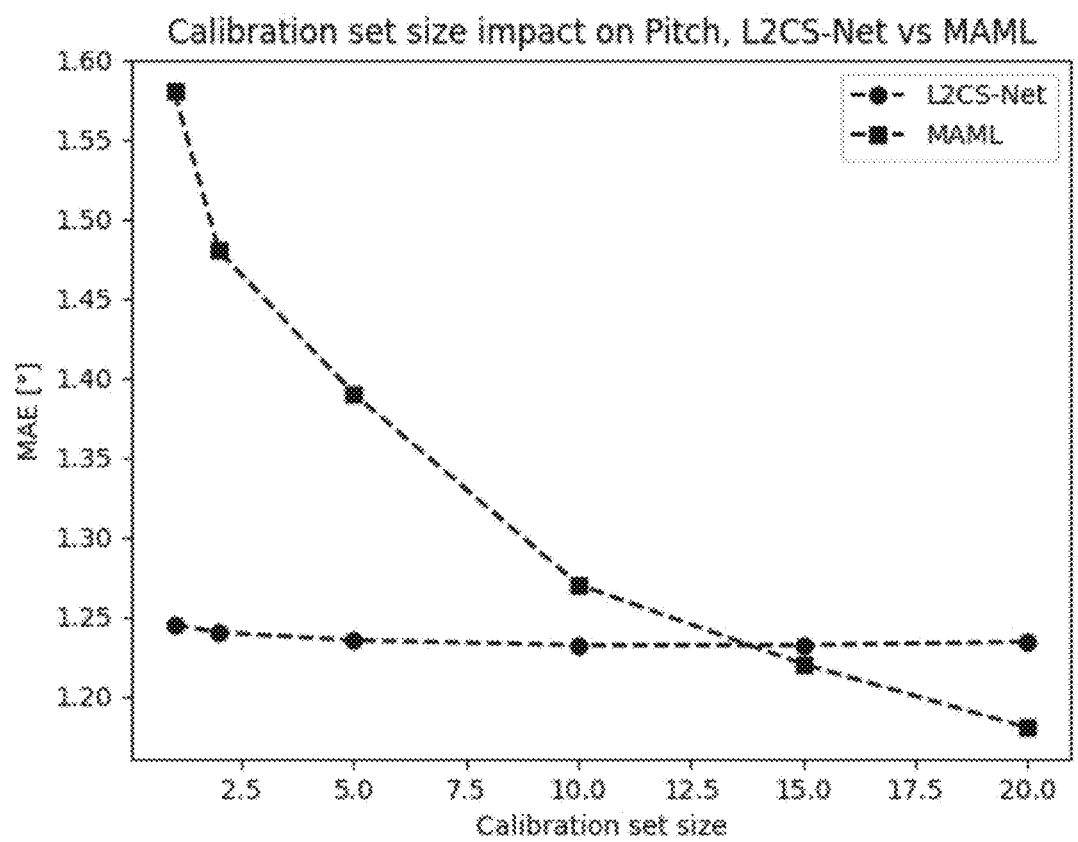
FIGS. 9A-B are graphs showing the effects of pitch and yaw with respect to L2CS-Net and MAML techniques based on the number of calibration data points.
Figure 9B:
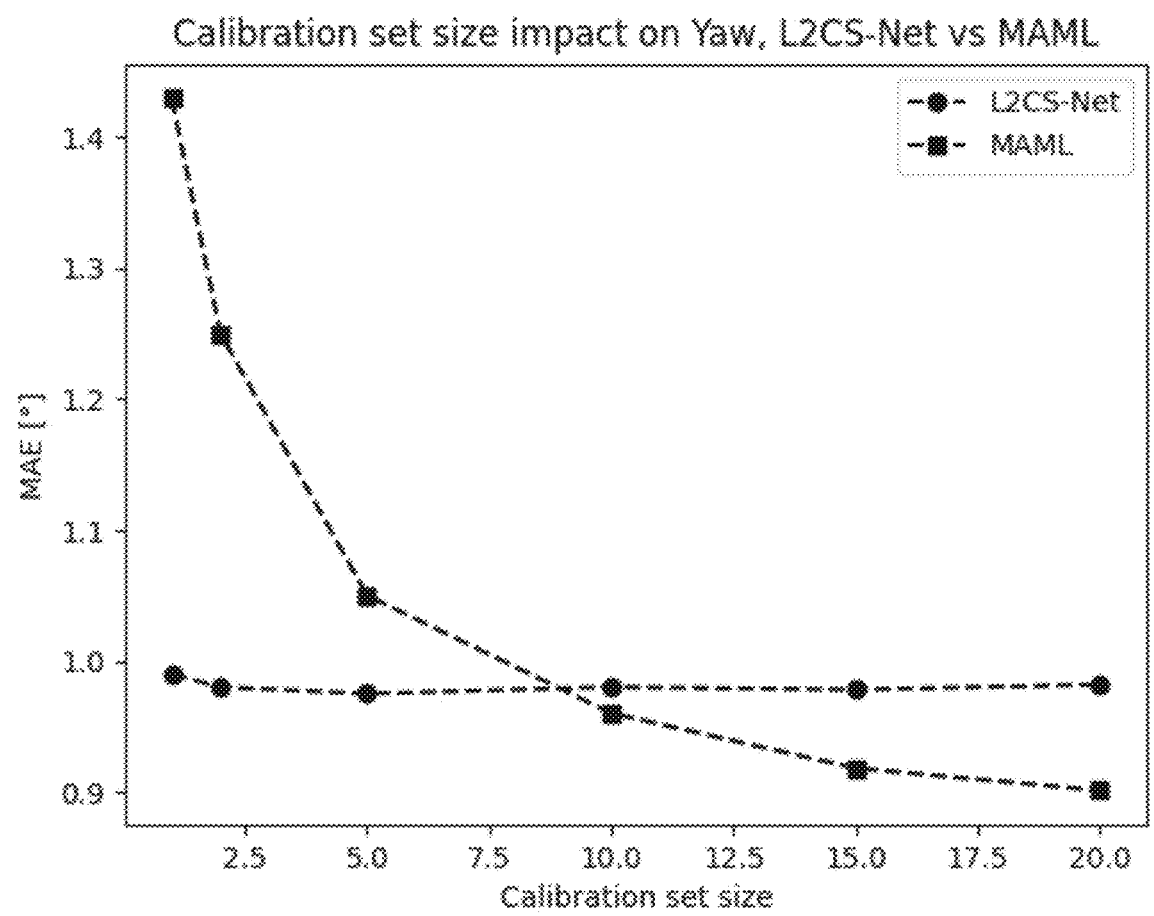

FIGS. 9A-B are graphs showing the effects of pitch and yaw with respect to L2CS-Net and MAML techniques based on the number of calibration data points. That is, FIG. 9 is an overview of a fine-tuning process for user specific neural network usage. As shown, MAML becomes more accurate after around 15 calibration data points for pitch, and 10 calibration data points for yaw.

The present disclosure may allow a positive impact on the fine-tuning, while standard training with gradient back-propagation is not generally susceptible to such a calibration process.

FIG. 9 Legend and Explanation:
  MAML: Abdelrahman et al. (2022) network with our modifications trained in our innovative way.
  L2CS-Net: Abdelrahman et al. (2022) network without any modifications, trained with standard gradient back-propagation method.
  Calibration set size: number of calibration data points used in the Adaptation phase.
  MAE: Mean absolute error (degrees).

In this embodiment, 15 calibration samples are enough to provide better performance for calibration than a network trained by traditional methods as measured by MAE.

Figure 10:
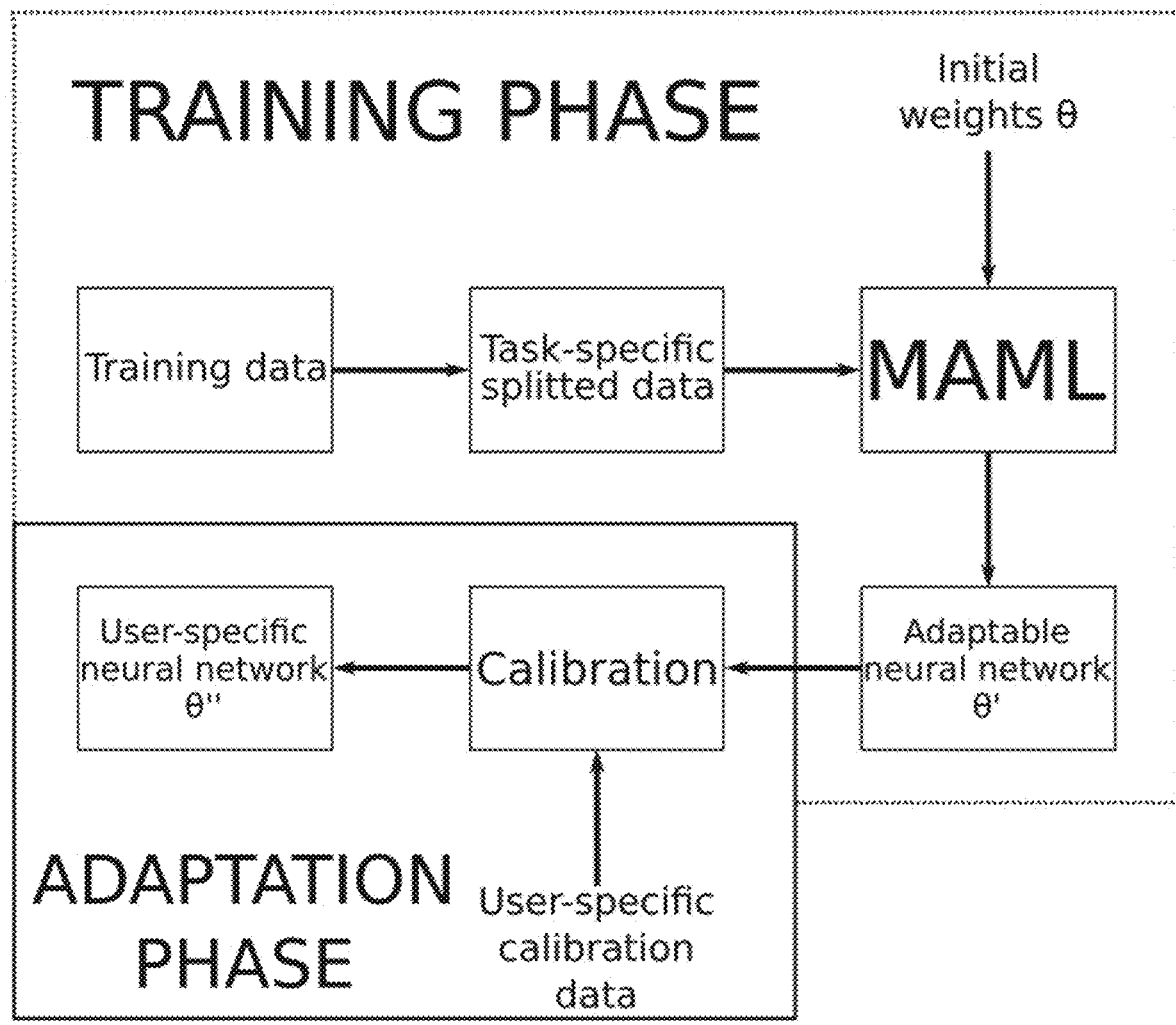
FIG. 10 is a block diagram of one embodiment of a training and adaptation phase.

FIG. 10 is a block diagram of one embodiment of a training and adaptation phase.

The training phase 1005 may be performed once per network, while the adaptation phase 1010 may be repeated for every user. Training phase 1005 may be performed offline and may require more memory than the adaptation phase 1010. Adaptation phase 1010 may be faster and less memory-consuming and may be performed many times for different users. The final product is the neural network with parameters θ", calibrated for the given user.

In this embodiment, the training phase 1005 may be parametrized as follows:

| Block | Parameter | Explanation |
| --- | --- | --- |
| Train Dataloader | Support set size | N/A |
| Train Dataloader | Query set size | N/A |
| Inner optimization | θ | Initial network weights |
| Inner optimization | j | Number of inner optimization steps |
| Inner optimization | α | Learning ratio |
| Meta optimization | β | Learning ratio |

In this embodiment, the adaptation phase 1010 may be parametrized as follows:

| Block | Parameter | Explanation |
| --- | --- | --- |
| User-specific optimization | θ' | Initial meta-network weights |
| User-specific optimization | j | Number of optimization steps |
| User-specific optimization | α | Learning ratio |

In this embodiment, the adaptation phase 1005 may utilize a standard backpropagation training.

Figure 11:
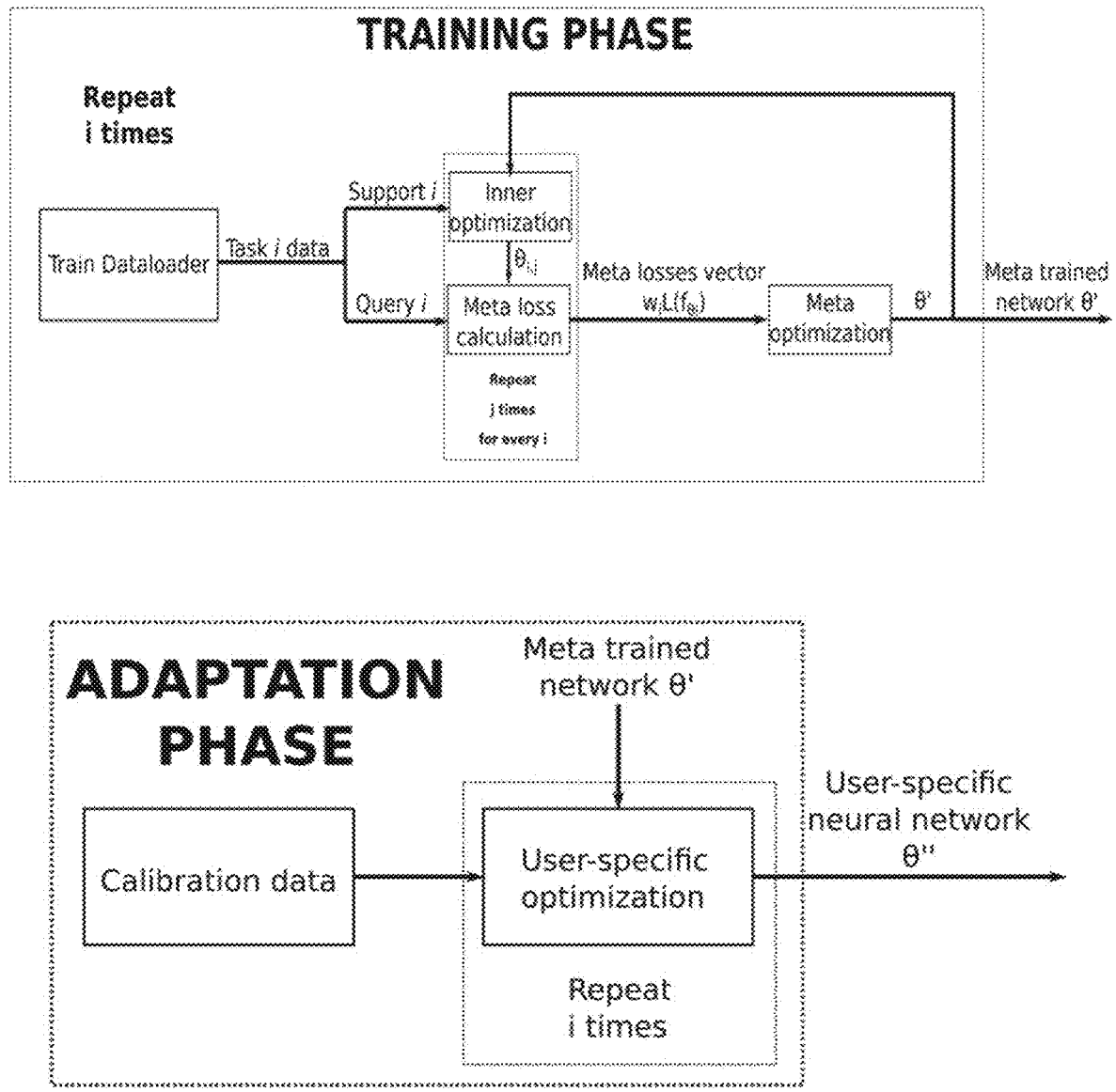
FIG. 11 is a block diagram of one embodiment of a training and adaptation phase.

FIG. 11 is a block diagram of one embodiment of a training and adaptation phase.

The training phase 1101 may be performed once per network, while the adaptation phase 1110 may be repeated for every user, similar to as shown in FIG. 10.

Figure 12:
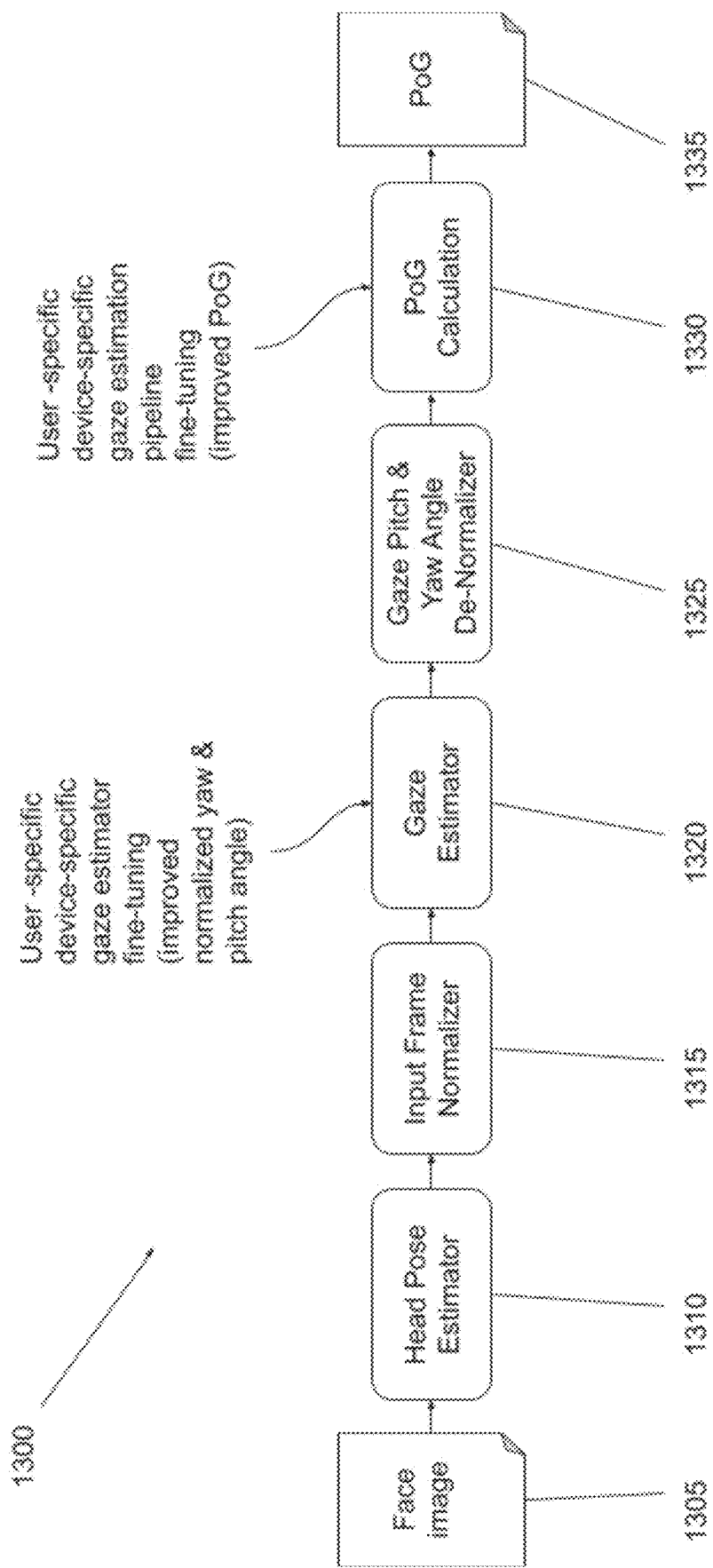
FIG. 12 is a flow diagram of one embodiment of a method of determining point of gaze.

FIG. 12 is a flow diagram of one embodiment of a method of determining point of gaze. As shown in FIG. 12, the method of determining point of gaze 1300, may comprise starting with a face image 1305, processing the face image with a head pose estimator 1310, processing with an input frame normalizer 1315, processing with a gaze estimator 1320, processing with a gaze pitch & yaw angle de-normalizer 1325, using a PoG calculation 1330, and determining PoG 1335.

In this embodiment, the gaze estimator 1320 may utilize a user-specific device specific gaze estimator fine-tuning method, which may provide an improved normalized yaw & pitch angle. In this embodiment, the PoG calculation 1330, may utilize a user-specific and device specific gaze estimation pipeline fine-tuning, which may provide an improved PoG.

Figure 13:
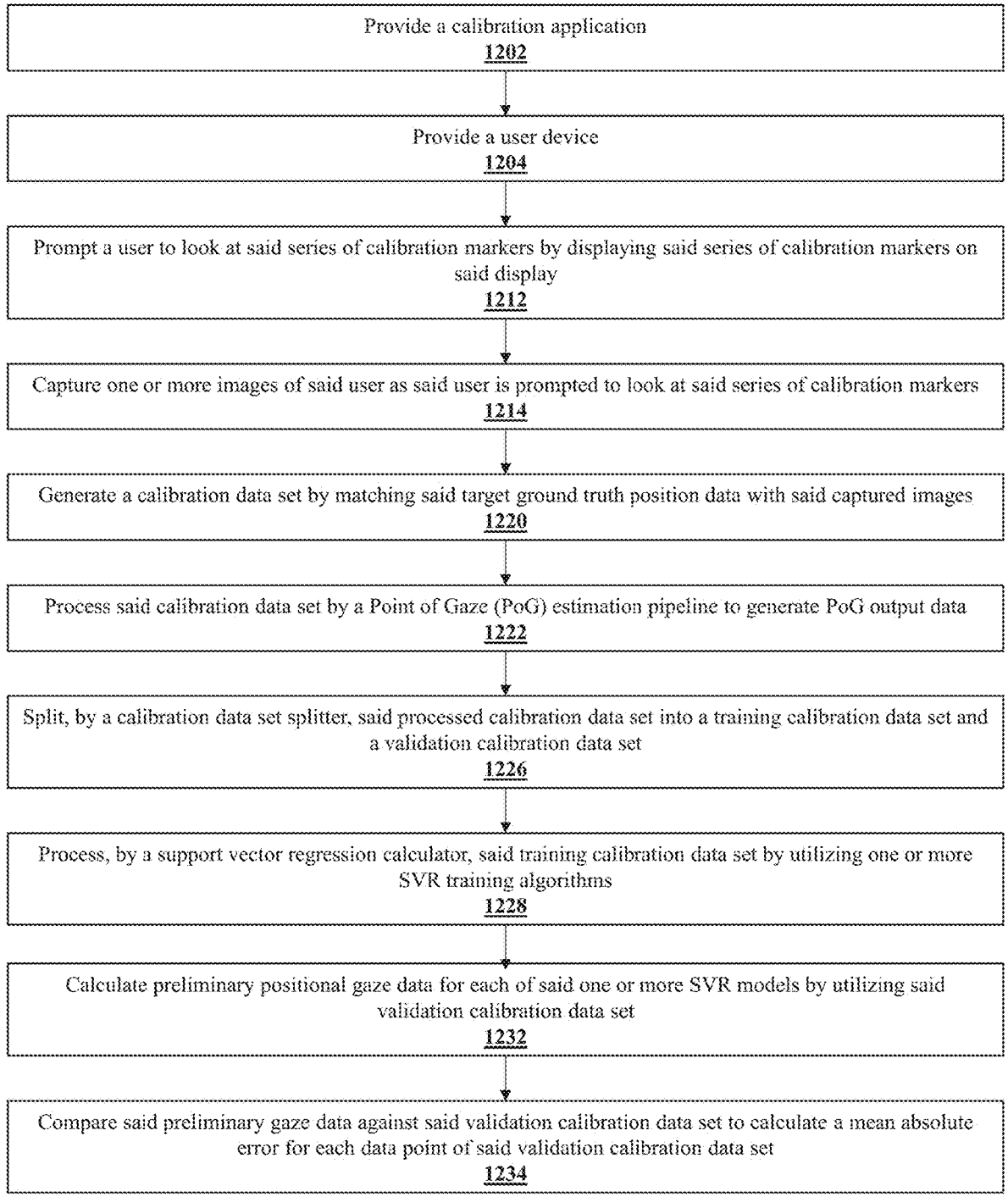
FIG. 13 is a flow diagram of one embodiment of a method of calibrating point of gaze estimation.

FIG. 13 is a flow diagram of one embodiment of a method of calibrating point of gaze estimation 1200, comprising the steps: providing a calibration application 1202; and providing a user device 1204. In one embodiment, the user device may comprise a display and a user-facing camera. In one embodiment, the calibration application may run on the user device. In one embodiment, the calibration application may cause to be displayed on the display a series of calibration markers. In one embodiment, the calibration application may prompt a user to look at the series of calibration markers by displaying the series of calibration markers on the display 1212. In one embodiment, the calibration application may capture one or more images of the user as the user is prompted to look at the series of calibration markers 1214. In one embodiment, a series of coordinates on the display may be recorded for each of the series of calibration markers. In one embodiment, the series of coordinates may comprise a series of target ground truth positions for the series of calibration markers. In one embodiment, the calibration application may generate a calibration data set by matching the target ground truth position data with the captured images 1220. In one embodiment, the calibration application may process the calibration data set by a Point of Gaze ("PoG") estimation pipeline to generate PoG output data 1222. In one embodiment, the target ground truth position data and PoG output data comprise a processed calibration data set. In one embodiment, the calibration application may be split, by a calibration data set splitter, the processed calibration data set into a training calibration data set and a validation calibration data set 1226. In one embodiment, the calibration application may process, by a support vector regression calculator, the training calibration data set by utilizing one or more SVR training algorithms 1228. In one embodiment, the one or more SVR training algorithms may be used to generate one or more SVR models after processing the training calibration data set. In one embodiment, the calibration application may calculate preliminary positional gaze data for each of the one or more SVR models by utilizing the validation calibration data set 1232. In one embodiment, the calibration application may compare the preliminary gaze data against the validation calibration data set to calculate a mean absolute error for each data point of the validation calibration data set 1234. In one embodiment, a best SVR model may be selected from the one or more SVR models based on which of the SVR model has a lowest mean absolute error. In one embodiment, the validation calibration data set may be used to calculate preliminary positional gaze data for each of the several SVR models; wherein the preliminary gaze data can be compared against the validation calibration data set to calculate a mean absolute error for each data point of the validation calibration data set; wherein the best SVR model is determined from the several SVR models based on the individual SVR model with a lowest mean absolute error. In one embodiment, the best SVR model fine-tunes the preliminary gaze data.

Figure 14:
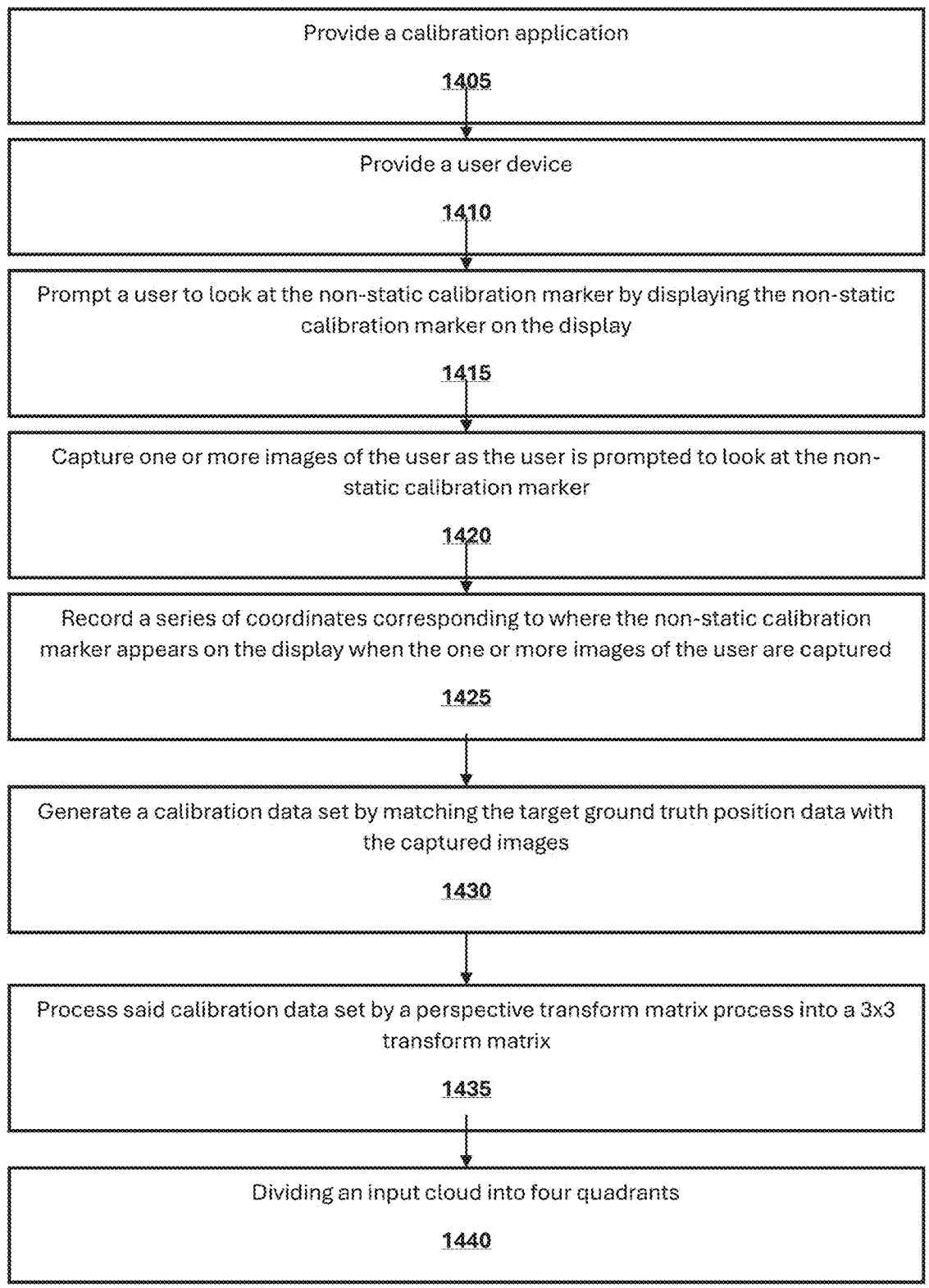
FIG. 14 is a flow diagram showing one embodiment of a method of calibrating point of gaze estimation.

FIG. 14 is a flow diagram showing one embodiment of a method of calibrating point of gaze estimation. As shown in FIG. 14, the method of calibrating point of gaze estimation 1400 may comprise the steps, providing a calibration application 1405, providing a user device 1410; prompting a user to look at said non-static calibration marker by displaying said non-static calibration marker on said display 1415; capturing one or more images of said user as said user is prompted to look at said non-static calibration marker 1420; recording a series of coordinates corresponding to where said non-static calibration marker appears on said display when said one or more images of said user are captured 1425; generating a calibration data set by matching said target ground truth position data with said captured images 1430; processing said calibration data set by a perspective transform matrix process into a 3×3 transform matrix 1435; and dividing an input cloud into four quadrants, wherein said input cloud comprises said look points 1440.

In some embodiments the user device may comprise a display and a user-facing camera.

In some embodiments the calibration application may run on the user device.

In some embodiments the calibration application may cause to be displayed on the display a non-static calibration marker. In one embodiment, the non-static calibration marker may move on the display in a continuous movement at a substantially consistent speed. In other embodiments, the non-static calibration marker may have a variable speed or make one or more starts and stops along the path taken. In some embodiments, the non-static calibration marker may follow a pre-determined path, as described hereinbelow, or may take a random path.

In some embodiments the series of coordinates may comprise a series of target ground truth positions for the non-static calibration marker, which may comprise a target ground truth position data.

In some embodiments the target ground truth position data may comprise one or more vertices. The vertices may comprise four vertices a first vertex, a second vertex, a third vertex, and a fourth vertex. The vertices, if connected, may form a quadrangle.

In some embodiments the vertices may be in a top left display corner, a top right display corner, the third vertex is a bottom-left display corner, and the fourth vertex is a bottom right display corner.

In some embodiments, where the user is determined to have been looking is a look point, and this information may be used for calibration purposes.

In some embodiments a center point of the four quadrants may comprise a center of mass of the look points. For example, the look points may be plot on a coordinate plane, which may then be divided into quadrants, the center point of which may be determined based on a weighted measurement of the look points.

In some embodiments the vertices are determined to produce a quadrangle of the largest area for a given quadrant.

In some embodiments, the use of a non-static calibration marker may be used in a pattern that may cover the entire display area and produce a consistent estimated point of gaze point cloud, which may be used to calculate a calibration mapping function as a perspective transform matrix that applies calibration algorithms to stretch un-calibrated point of gaze estimations into a point cloud that covers the whole display. In a preferred embodiment, the animated pattern includes four vertices, which may be identified, that apply to four vertices of a display, such as top-left, top-right, bottom-left, and bottom-right corners. There may be multiple sets of four vertices for a given display. In a preferred embodiment, the input point cloud may be divided into four quadrants based on a center of mass of the input point cloud.

Figure 15A:
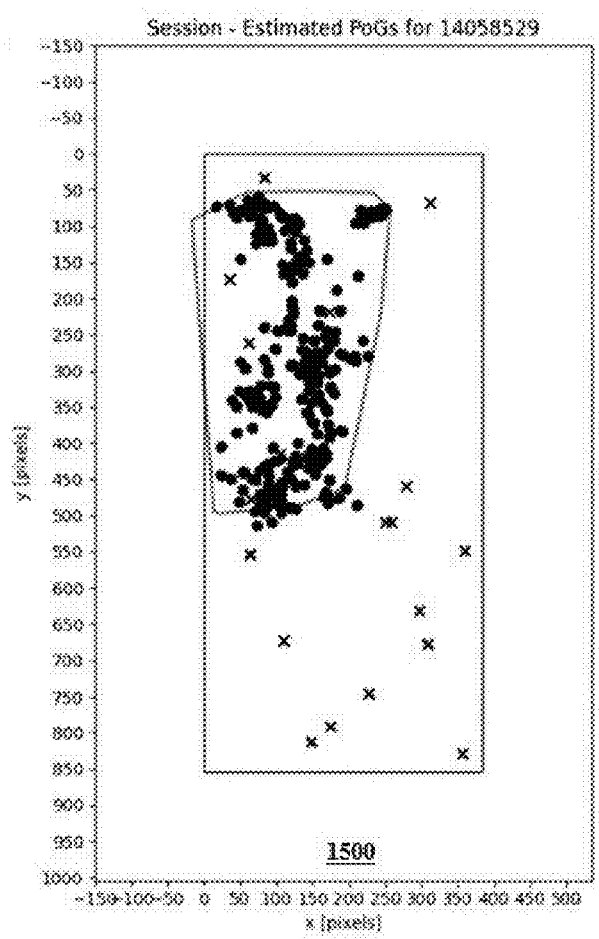
FIG. 15A is a chart showing gaze data output that is un-calibrated.

FIG. 15A is one embodiment of a chart showing gaze data output that is un-calibrated. As shown in FIG. 15A, uncalibrated data output does not appear to closely match where the markers were 1500.

Figure 15B:
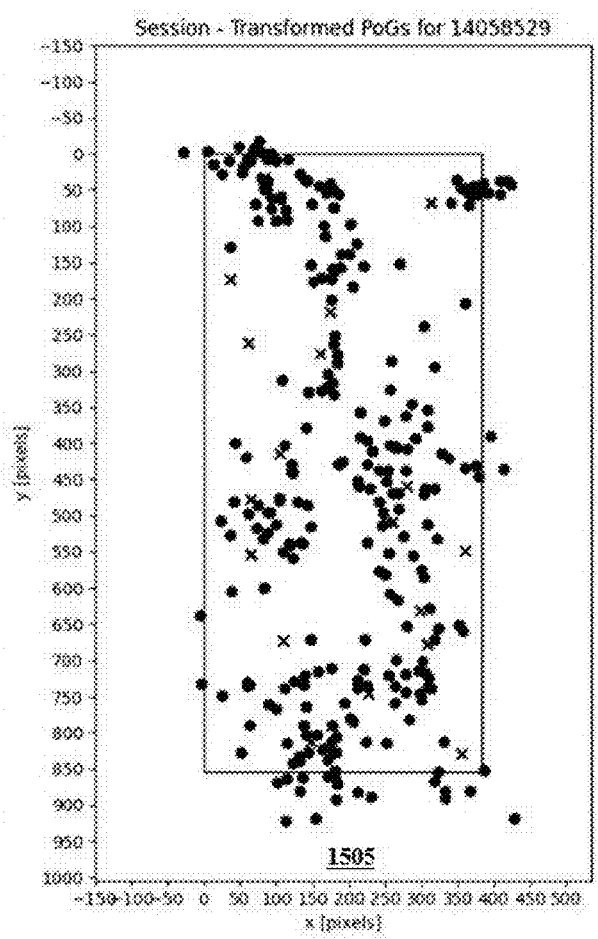
FIG. 15B is a chart showing gaze data output that is calibrated.

FIG. 15B is one embodiment of a chart showing gaze data output that is calibrated. As shown in FIG. 15B, data that has been calibrated via a point of gaze estimation pipeline. As shown in FIG. 15B, this data may more closely match where the markers were compared to an uncalibrated data output, but it includes data points that appear inaccurate or may be outliers 1505.

Figure 16:
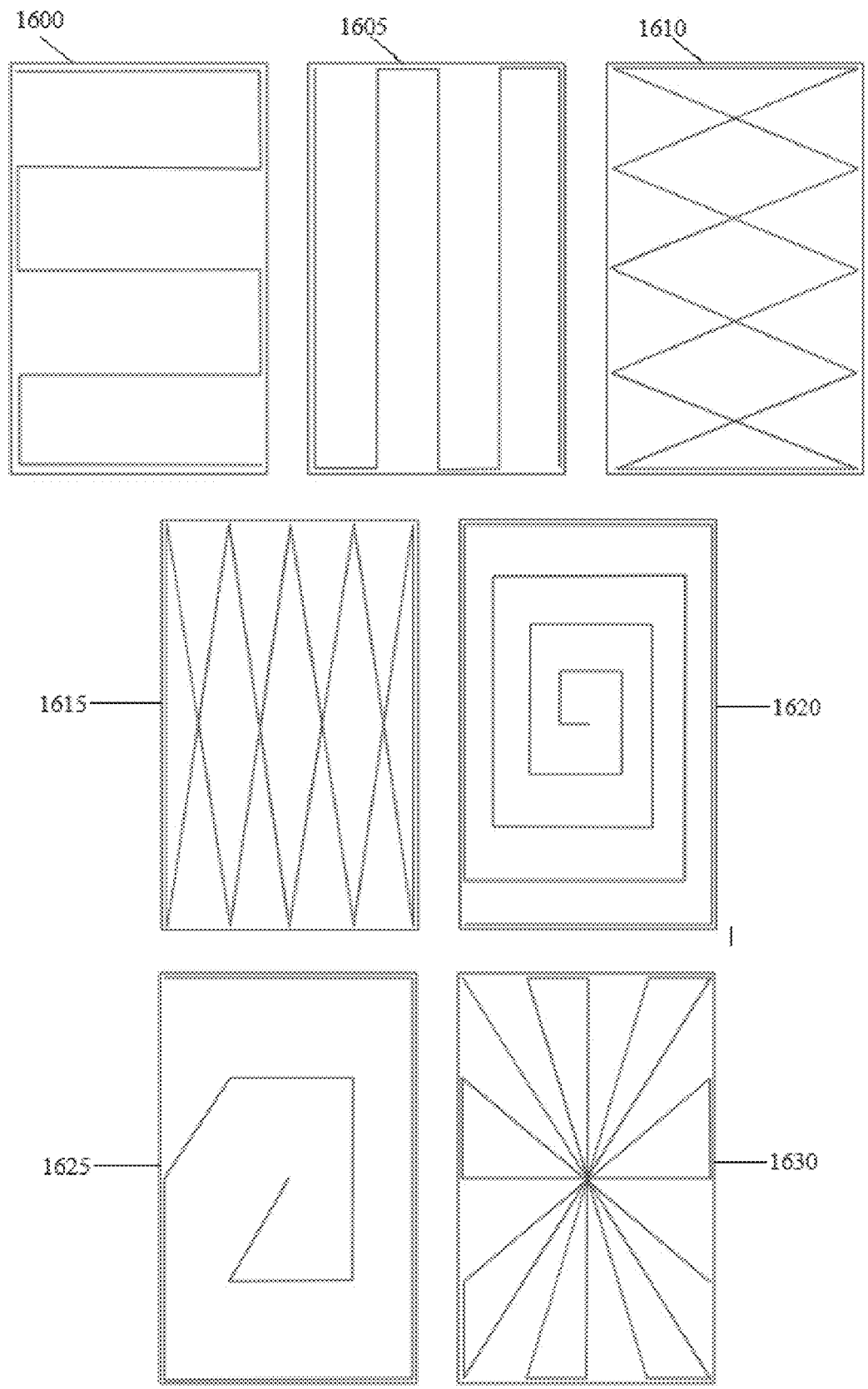
FIG. 16 is a series of patterns that a non-static calibration marker may move along for the present disclosure.

FIG. 16 is a series of patterns that a non-static calibration marker may move along for the present disclosure. As shown in FIG. 16, the patterns that a non-static calibration marker may move along may be a myriad of potential shapes and routes and be referred to as animated patterns, in some embodiments. The patterns may preferably include points at various locations on a display, and may include corners of the display device used. Some of the patterns may be referred to as horizontal zig-zag 1600, vertical zig-zag 1605, horizontal saw 1610, vertical saw 1615, 13-point 1620, spiral 1625, and star 1630, as shown in FIG. 16.

Figure 17:
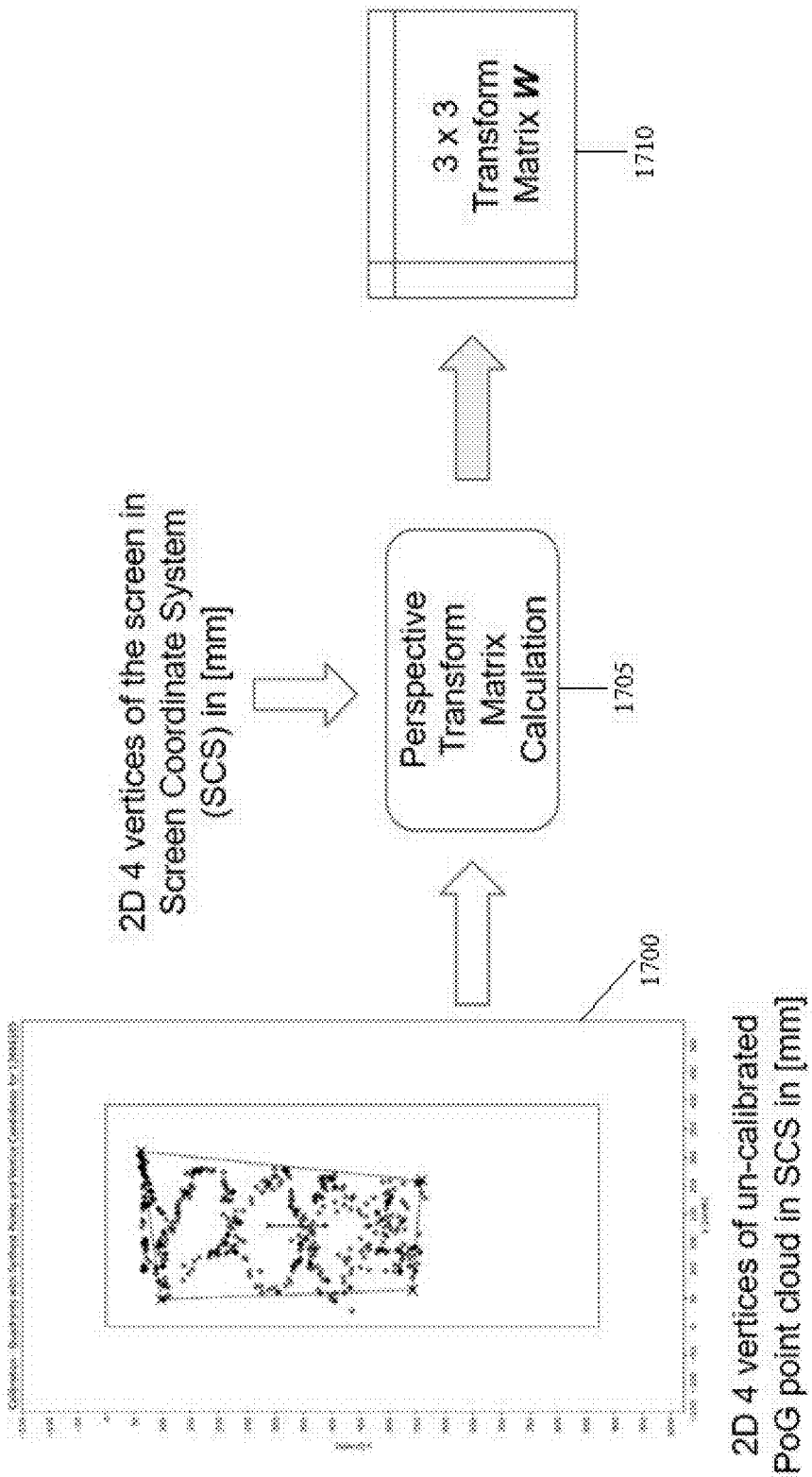
FIG. 17 is a diagram showing a process for conducting a perspective transform matrix on un-calibrated gaze data output.

FIG. 17 is a diagram showing a process for conducting a perspective transform matrix on un-calibrated gaze data output 1700. As shown in FIG. 17, when processed through a perspective transform matrix 1705, the un-calibrated gaze data output may generate a 3×3 Transform Matrix W 1710.

In one embodiment, the perspective transform matrix may be a 3×3 matrix of float values that define how a given 2D PoG point (x, y) outputted from an un-calibrated gaze estimation pipeline is transformed into a "fine-tuned" PoG point (x", y"). In one embodiment, the following formula may be used:

$$\begin{pmatrix} x' \\ y' \\ 1 \end{pmatrix} = \underbrace{\begin{pmatrix} a & b & c \\ d & e & f \\ g & h & i \end{pmatrix}}_{W} \begin{pmatrix} x \\ y \\ 1 \end{pmatrix} \quad (1)$$

In one embodiment, i may be set to 1. Then, to find W, a further set of equations may be used as follows:

Assuming that 4 vertices are being transformed from an un-calibrated PoG point cloud, which may comprise the data output, the following equation:

$$A = (x_a, y_a), \qquad (2)$$
$$B = (x_b, y_b),$$
$$C = (x_c, y_c),$$
$$D = (x_d, y_d)$$

Into 4 vertices of the display:

$$A' = (x'_a, y'_a), \qquad (3)$$
$$B' = (x'_b, y'_b),$$
$$C' = (x'_c, y'_c),$$
$$D' = (x'_d, y'_d)$$

And for A $$x'_a = \frac{a \cdot x_a + b \cdot y_a + c}{g \cdot x_a + h \cdot y_a + 1} \qquad (6)$$

$$y'_a = \frac{d \cdot x_a + e \cdot y_a + f}{g \cdot x_a + h \cdot y_a + 1} \qquad (7)$$

The process described hereinabove may be repeated for determining additional vertices, such as B, C, and D.

In this embodiment, if it is assumed that i=1, then that creates a system of 8 equations (2 for each point) to solve for a, b, c, d, e, f, g, & h.

In order to solve the above set of equations, one embodiment may use widely available systems, such as OpenCV's getPerspectiveTransform( ) method or SVD implementation from NumPy package. In an alternative embodiment, other software may be quickly developed and implemented based on known methods.

In one embodiment, a Python pseudo-code for finding W may be as follows:

```
src = np.array([[x_a, y_a], [x_b, y_b], [x_c, y_c], [x_d, y_d]])
dst = np.array([[x'_a, y'_a], [x'_b, y'_b], [x'_c, y'_c], [x'_d, y'_d]])
matrix = [ ]
for (x, y), (xp, yp) in zip(src, dst):
    matrix.append([x, y, 1, 0, 0, 0, -xp*x, -xp*y, -xp])
    matrix.append([0, 0, 0, x, y, 1, -yp*x, -yp*y, -yp])
A = np.array(matrix, dtype=np.float)
_, _, Vt = np.linalg.svd(A)
W = Vt[-1].reshape(3, 3)   # Take the last row of the V matrix and reshape it
W = W / W[2, 2]    # Normalize the matrix
```

Figure 18:
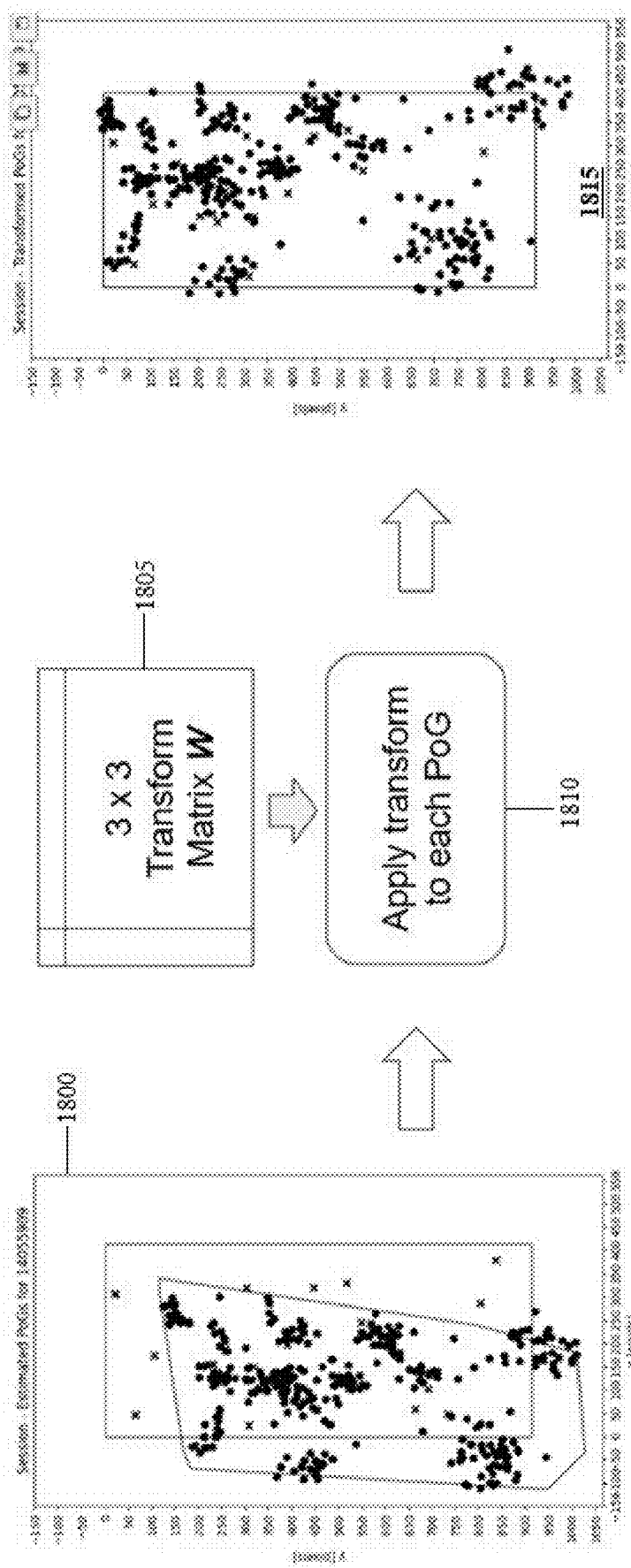
FIG. 18 is a diagram showing the effect of conducting a perspective transform matrix on un-calibrated gaze data output.

FIG. 18 is a diagram showing the effect of conducting a perspective transform matrix on un-calibrated gaze data output 1800. As shown in FIG. 18, applying the 3×3 transform matrix W 1805 to each Point of Gaze data output 1810 may result in more accurate gaze mapping 1815.

Some portions of the preceding detailed descriptions have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it should be appreciated that throughout the present disclosure, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system's memories or registers or other such information storage, transmission or display devices.

The processes or methods depicted in the figures may be performed by processing logic that comprises hardware (e.g., circuitry, dedicated logic, etc.), firmware, software (e.g., embodied on a non-transitory computer readable medium), or a combination thereof. Although the processes or methods are described above in terms of some sequential operations, it should be appreciated that some of the operations described may be performed in a different order. Moreover, some operations may be performed in parallel rather than sequentially.

In addition, the various illustrative logical blocks, modules, and circuits described in connection with certain embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, system-on-a-chip, or state machine. A processor may also be implemented as a combination of computing devices, e.g., a combination of a DSP and a microprocessor, a plurality of microprocessors, one or more microprocessors in conjunction with a DSP core, or any other such configuration.

Operational embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor may read information from, and write information to, the storage medium. In the alternative, the storage medium may be integral to the processor. The processor and the storage medium may reside in an ASIC or may reside as discrete components in another device.

Furthermore, the one or more versions may be implemented as a method, apparatus, or article of manufacture using standard programming and/or engineering techniques to produce software, firmware, hardware, or any combination thereof to control a computer to implement the disclosed embodiments. Non-transitory computer readable media may include but are not limited to magnetic storage devices (e.g., hard disk, floppy disk, magnetic strips), optical disks (e.g., compact disk (CD), digital versatile disk (DVD)), smart cards, and flash memory devices (e.g., card, stick). Those skilled in the art will recognize many modifications may be made to this configuration without departing from the scope of the disclosed embodiments.

The foregoing description of the preferred embodiment has been presented for the purposes of illustration and description. While multiple embodiments are disclosed, still other embodiments will become apparent to those skilled in the art from the above detailed description, which shows and describes the illustrative embodiments. As will be realized, these embodiments are capable of modifications in various obvious aspects, all without departing from the spirit and scope of the present disclosure. Accordingly, the detailed description is to be regarded as illustrative in nature and not restrictive. Also, although not explicitly recited, one or more additional embodiments may be practiced in combination or conjunction with one another. Furthermore, the reference or non-reference to a particular embodiment shall not be interpreted to limit the scope of protection. It is intended that the scope of protection not be limited by this detailed description, but by the claims and the equivalents to the claims that are appended hereto.

Except as stated immediately above, nothing which has been stated or illustrated is intended or should be interpreted to cause a dedication of any component, step, feature, object, benefit, advantage, or equivalent to the public, regardless of whether it is or is not recited in the claims.

What is claimed is:

1. A method of calibrating point of gaze estimation, comprising the steps:
    providing a calibration application;
    providing a user device;
    wherein said user device comprises a display and a user-facing camera;
    wherein said calibration application runs on said user device;
    wherein said calibration application causes to be displayed on said display a non-static calibration marker;
    prompting a user to look at said non-static calibration marker by displaying said non-static calibration marker on said display;
    capturing one or more images of said user as said user is prompted to look at said non-static calibration marker;
    recording a series of coordinates corresponding to where said non-static calibration marker appears on said display when said one or more images of said user are captured;
    wherein said series of coordinates comprise a series of target ground truth positions for said non-static calibration marker, which comprise a target ground truth position data;
    generating a calibration data set by matching said target ground truth position data with said captured images; and
    processing said calibration data set by a perspective transform matrix process into a 3×3 transform matrix.

2. The method of calibrating point of gaze estimation of claim 1, wherein said target ground truth position data comprises one or more vertices.

3. The method of calibrating point of gaze estimation of claim 2, wherein said one or more vertices comprise four vertices.

4. The method of calibrating point of gaze estimation of claim 3, wherein said four vertices comprise a first vertex, a second vertex, a third vertex, and a fourth vertex; and
    wherein said one or more vertices, if connected, form a quadrangle.

5. The method of calibrating point of gaze estimation of claim 4, wherein said first vertex is a top left display corner;
    wherein said second vertex is a top right display corner;
    wherein said third vertex is a bottom left display corner; and
    wherein said fourth vertex is a bottom right display corner.

6. The method of calibrating point of gaze estimation of claim 5, wherein where said user is determined to have been looking is a look point;
    dividing an input cloud into four quadrants, wherein said input cloud comprises said look points.

7. The method of calibrating point of gaze estimation of claim 6, wherein a center point of said four quadrants comprises a center of mass of said look points.

8. The method of calibrating point of gaze estimation of claim 7, wherein said vertices are determined to produce a quadrangle of the largest area for a given quadrant.

9. The method of calibrating point of gaze estimation of claim 8, wherein said user comprises one or more user characteristics;
    wherein said one or more user characteristics comprise gender, skin color, eye shape, age, hair, background color, and lighting conditions; and
    wherein said user characteristics are used as factors in said perspective transform matrix.

10. A method of calibrating point of gaze estimation, comprising the steps:
    providing a calibration application;
    providing a user device;
    wherein said user device comprises a display and a user-facing camera;
    wherein said calibration application runs on said user device;
    wherein said calibration application causes to be displayed on said display a non-static calibration marker;
    prompting a user to look at said non-static calibration marker by displaying said non-static calibration marker on said display;
    capturing one or more images of said user as said user is prompted to look at said non-static calibration marker;
    recording a series of coordinates corresponding to where said non-static calibration marker appears on said display when said one or more images of said user are captured;
    wherein said series of coordinates comprise a series of target ground truth positions for said non-static calibration marker, which comprise a target ground truth position data;
    generating a calibration data set by matching said target ground truth position data with said captured images;
    processing said calibration data set by a perspective transform matrix process into a 3×3 transform matrix;
    wherein said target ground truth position data comprises one or more vertices;
    wherein said one or more vertices comprise four vertices;
    wherein said four vertices comprise a first vertex, a second vertex, a third vertex, and a fourth vertex;

wherein said one or more vertices, if connected, form a quadrangle;
wherein said first vertex is a top left display corner;
wherein said second vertex is a top right display corner;
wherein said third vertex is a bottom left display corner;
wherein said fourth vertex is a bottom right display corner;
wherein where said user is determined to have been looking is a look point;
dividing an input cloud into four quadrants, wherein said input cloud comprises said look points;
wherein a center point of said four quadrants comprises a center of mass of said look points;
wherein said vertices are determined to produce a quadrangle of the largest area for a given quadrant.

* * * * *